United States Patent
Klein

(10) Patent No.: US 11,464,934 B2
(45) Date of Patent: *Oct. 11, 2022

(54) GAS DELIVERY METHOD AND APPARATUS

(71) Applicant: THORNHILL SCIENTIFIC INC., Toronto (CA)

(72) Inventor: Michael Klein, Toronto (CA)

(73) Assignee: THORNHILL SCIENTIFIC INC., North York (CA)

( * ) Notice: Subject to any disclaimer, the term of this patent is extended or adjusted under 35 U.S.C. 154(b) by 424 days.

This patent is subject to a terminal disclaimer.

(21) Appl. No.: 16/781,665

(22) Filed: Feb. 4, 2020

(65) Prior Publication Data
US 2020/0276406 A1    Sep. 3, 2020

Related U.S. Application Data

(63) Continuation of application No. 15/405,069, filed on Jan. 12, 2017, now Pat. No. 10,576,238, which is a (Continued)

(51) Int. Cl.
*A61M 16/12* (2006.01)
*G05D 11/13* (2006.01)
(Continued)

(52) U.S. Cl.
CPC ........ *A61M 16/12* (2013.01); *A61M 16/0051* (2013.01); *A61M 16/026* (2017.08);
(Continued)

(58) Field of Classification Search
CPC .............. A61M 16/00; A61M 16/0051; A61M 16/024; A61M 16/026; A61M 16/103;
(Continued)

(56) References Cited

U.S. PATENT DOCUMENTS 5,094,235 A   3/1992  Westenskow et al.
5,320,093 A   6/1994  Raemer
(Continued)

FOREIGN PATENT DOCUMENTS

CN   201399147   2/2010
CN   101829386   9/2010
(Continued)

OTHER PUBLICATIONS

CIPO, Examination Report, dated Nov. 23, 2018, re Canadian Patent Application No. 2833018.
(Continued)

*Primary Examiner* — Joseph D. Boecker
(74) *Attorney, Agent, or Firm* — Perry + Currier Inc.

(57) ABSTRACT

An apparatus, method and system for delivering $CO_2$ into an inspiratory gas stream to formulate a blended respiratory gas in a manner that continuously maintains a target $CO_2$ concentration in a volume of the inspired respiratory gas, for example, over the course of a breath or a volumetrically definable part thereof or a series of partial or full breaths.

16 Claims, 7 Drawing Sheets

Related U.S. Application Data continuation of application No. 14/111,993, filed as application No. PCT/CA2012/000351 on Apr. 12, 2012, now Pat. No. 9,555,209.

(60) Provisional application No. 61/475,106, filed on Apr. 13, 2011.

(51) Int. Cl.
*A61M 16/20* (2006.01)
*A61M 16/00* (2006.01)
*A61M 16/10* (2006.01)

(52) U.S. Cl.
CPC .......... *A61M 16/20* (2013.01); *A61M 16/203* (2014.02); *G05D 11/138* (2013.01); *A61M 2016/0036* (2013.01); *A61M 2016/0039* (2013.01); *A61M 2016/102* (2013.01); *A61M 2016/103* (2013.01); *A61M 2202/0225* (2013.01); *A61M 2205/18* (2013.01); *A61M 2205/3334* (2013.01); *A61M 2205/50* (2013.01); *A61M 2205/502* (2013.01); *A61M 2230/432* (2013.01)

(58) Field of Classification Search
CPC .. A61M 16/12; A61M 16/202; A61M 16/203; A61M 16/204; A61M 2016/0033; A61M 2016/0036; A61M 2016/0039; A61M 2016/102; A61M 2202/0225; A61M 2205/3334; A61M 2205/50; G05D 11/138
See application file for complete search history.

(56) References Cited

U.S. PATENT DOCUMENTS

| | | | |
|---|---|---|---|
| 5,540,233 A | 7/1996 | Larsson et al. | |
| 5,558,083 A | 9/1996 | Bathe et al. | |
| 5,918,596 A | 7/1999 | Heinonen | |
| 5,957,129 A | 9/1999 | Tham et al. | |
| 6,076,523 A | 6/2000 | Jones et al. | |
| 6,139,506 A | 10/2000 | Heinonen | |
| 6,216,690 B1* | 4/2001 | Keitel | A61M 16/026 128/204.21 |
| 6,983,750 B2 | 1/2006 | Heinonen | |
| 7,150,717 B2 | 12/2006 | Katura et al. | |
| 7,516,742 B2 | 4/2009 | Stenzler et al. | |
| 7,621,272 B2 | 11/2009 | Orr | |
| 7,959,443 B1 | 6/2011 | Frembgen et al. | |
| 8,459,258 B2 | 6/2013 | Slessarev et al. | |
| 8,789,524 B2* | 7/2014 | Oberle | A61M 16/12 128/200.24 |
| 9,555,209 B2* | 1/2017 | Klein | A61M 16/203 |
| 10,576,238 B2* | 3/2020 | Klein | G05D 11/138 |
| 2002/0169385 A1 | 11/2002 | Heinonen et al. | |
| 2002/0185126 A1 | 12/2002 | Krebs | |
| 2002/0185129 A1 | 12/2002 | Fisher et al. | |
| 2004/0144383 A1* | 7/2004 | Thomas | A61M 16/024 128/204.18 |
| 2007/0181126 A1 | 8/2007 | Tomie et al. | |
| 2007/0221224 A1 | 9/2007 | Pittman et al. | |
| 2009/0018373 A1 | 1/2009 | Werth et al. | |
| 2009/0120435 A1 | 5/2009 | Slessarev et al. | |
| 2009/0241960 A1 | 10/2009 | Tunnell et al. | |
| 2010/0224191 A1 | 9/2010 | Dixon et al. | |
| 2011/0023879 A1 | 2/2011 | Vandine et al. | |
| 2012/0215124 A1 | 8/2012 | Fisher et al. | |
| 2012/0272957 A1 | 11/2012 | Chapman et al. | |
| 2014/0158124 A1 | 6/2014 | L'her et al. | |
| 2015/0034085 A1 | 2/2015 | Klein et al. | |
| 2016/0128609 A1 | 5/2016 | Clemensen et al. | |

FOREIGN PATENT DOCUMENTS

| | | |
|---|---|---|
| DE | 10200505335 | 5/2007 |
| EP | 1238631 | 9/2002 |
| EP | 1923088 | 5/2008 |
| JP | H01-321508 A | 12/1989 |
| JP | H07-194705 A | 8/1995 |
| JP | 2002509005 A | 3/2002 |
| JP | 2006513004 A | 4/2006 |
| JP | 2012521252 A | 9/2012 |
| WO | WO-9211052 | 7/1992 |
| WO | WO-2010109364 A1 | 9/2010 |

OTHER PUBLICATIONS

EPO, Extended European Search Report, dated Dec. 5, 2014, re European Patent Application No. 12772038.1.
Hoskin et al.; "Inspired and expired gas concentrations in man during carbogen breathing"; Radiotherapy and Oncology 51; Jan. 5, 1999; pp. 175-177.
Ito et al.; "Non-invasive prospective targeting of arterial PCO2 in subjects at rest"; J Physiol 586.15; Jun. 19, 2008; pp. 3675-3682.
Mark et al.; "Improved fMRI calibration: Precisely controlled hyperoxic versus hypercapnic stimuli"; NeuroImage 54; Sep. 7, 2010; pp. 1102-1111.
Mark et al.; "Precise control of end-tidal carbon dioxide and oxygen improves BOLD and ASL cerebrovascular reactivity measures"; Magnetic Resonance in Medicine 64; Jul. 20, 2010; pp. 749-756.
Prisman et al.; "Modified oxygen mask to induce target levels of hyperoxia and hypercarbia during radiotherapy: A more effective alternative to carbogen"; Int. J. Radiat. Biol., vol. 83, No. 7; Jul. 2007; pp. 457-462.
Slessarev et al.; "Prospective targeting and control of end-tidal CO2 and O2 concentrations"; J Physiol 581.3; Apr. 5, 2007; pp. 1207-1219.
USPTO, Non-Final Rejection, dated Feb. 3, 2016, re U.S. Appl. No. 14/111,993.
USPTO, Non-Final Rejection, dated May 20, 2019, re U.S. Appl. No. 15/405,069.
USPTO, Notice of Allowance and Fees Due, dated Oct. 22, 2019, re U.S. Appl. No. 15/405,069.
USPTO, Notice of Allowance and Fees Due, dated Sep. 20, 2016, re U.S. Appl. No. 14/111,993.
CNIPA, First Office Action [with English translation], dated May 14, 2015, re Chinese Patent Application No. 201280028698.7.
CNIPA, Second Office Action [with English translation], dated Jan. 4, 2016, re Chinese Patent Application No. 201280028698.7.
EPO, Communication pursuant to Article 94(3) EPC, dated Apr. 8, 2020, re European Patent Application No. 12772038.1.
EPO, Communication pursuant to Article 94(3) EPC, dated Aug. 28, 2017, re European Patent Application No. 12772038.1.
ISA/CA, International Search Report and Written Opinion, dated Aug. 1, 2012, re PCT International Patent Application No. PCT/CA2012/000351.
JPO, Notice of Reasons for Refusal [with English translation], dated Mar. 22, 2016, re Japanese Patent Application No. 2014-504126.
JPO, Search Report [with English translation], dated Feb. 18, 2016, re Japanese Patent Application No. 2014-504126.
WIPO/IB, International Preliminary Report on Patentability (Ch.1), dated Oct. 24, 2013, re PCT International Patent Application No. PCT/CA2012/000351.

* cited by examiner

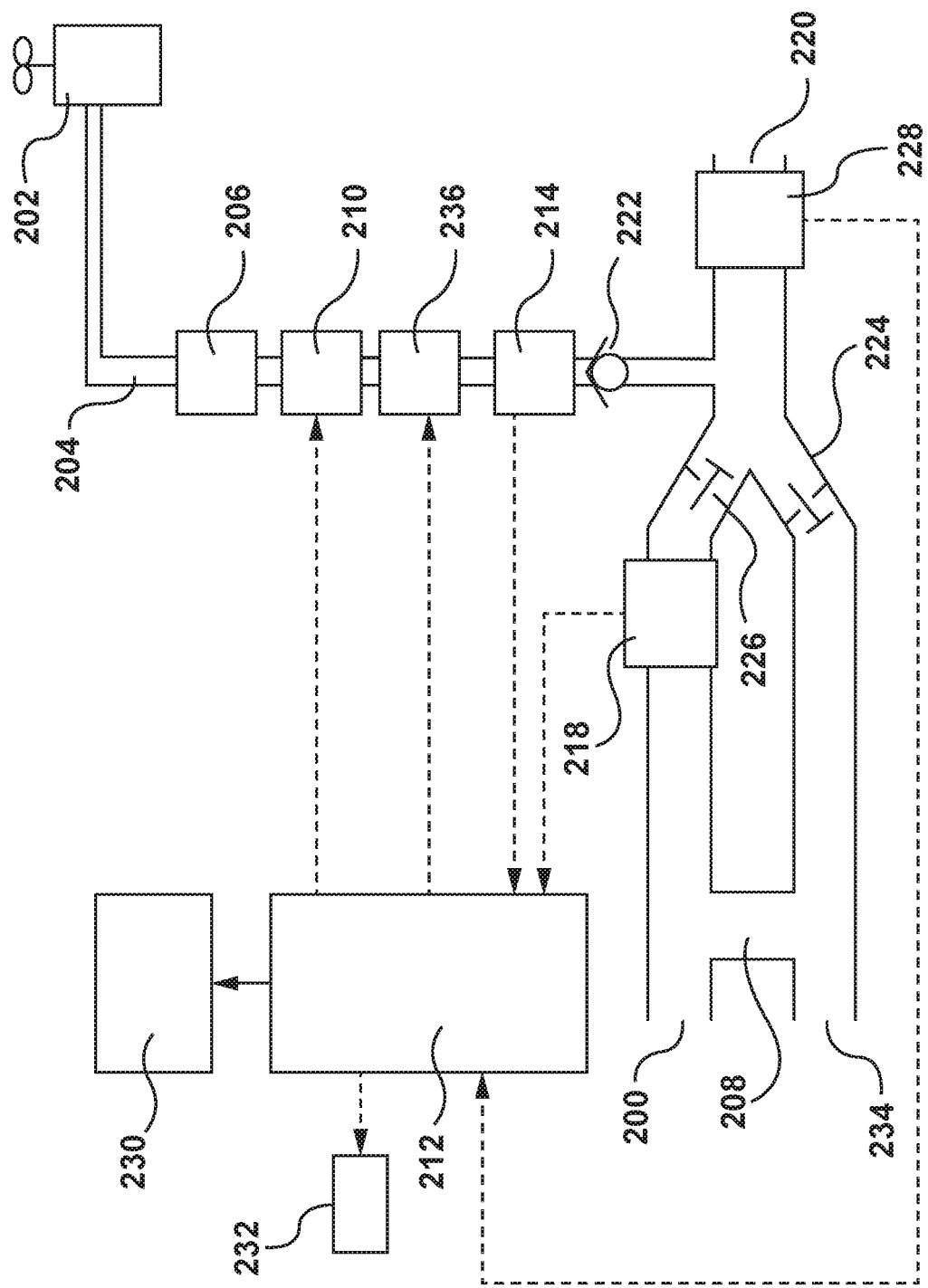

GAS DELIVERY METHOD AND APPARATUS

CROSS-REFERENCE TO RELATED APPLICATION

The present application is a continuation of co-pending U.S. patent application Ser. No. 14/111,993, filed Nov. 15, 2013, which is a national phase filing, under 35 U.S.C. § 371(c), of International Application No. PCT/CA2012/000351, filed Apr. 12, 2012, the disclosures of which are incorporated herein by reference as if set forth in full herein. International Application No. PCT/CA2012/000351, in turn, claims the benefit, under 35 U.S.C. § 119(e), of U.S. provisional application Ser. No. 61/475,106, filed on Apr. 13, 2011, the disclosure of which is incorporated herein by reference in its entirety.

FIELD OF THE INVENTION

The present invention relates to a device, method and system for delivering $CO_2$ into an inspiratory gas stream to formulate a blended respiratory gas in a manner that continuously maintains a target $CO_2$ concentration in a volume of the inspired respiratory gas, for example, over the course of a breath or a volumetrically definable part thereof or a series of partial or full breaths.

BACKGROUND OF THE INVENTION

The arterial partial pressure of $CO_2$ ($PaCO_2$) is intimately related to the acid base status of the blood. $CO_2$ combines with water to form carbonic acid. The higher the $PaCO_2$ the more acid is the blood. $CO_2$ is formed in the body by metabolism and is eliminated from the lungs by ventilation. The relationship between $PCO_2$ and ventilation is a rectangular hyperbola with $PCO_2$ becoming infinite at low ventilations and reaching an asymptote of 0 at infinite ventilation. Ventilation is therefore controlled in response to chemosensitive neurons located in the brainstem and surrounding major arteries.

There are many occasions where it is required to induce a change in $PaCO_2$ in a subject or patient. One example is to study the responses of various body systems to changes in $CO_2$ such as the chemoreceptor cells themselves, breathing pattern, arousal, brain blood flow, coronary artery blood flow, ocular blood flow, renal blood flow, changes in blood vessel diameter in various organs and major arteries such as the brachial artery, and changes in brain waves, behavior and seizure threshold. We pick brain blood flow, blood volume and oxygen extraction fraction as an example for the use of changes in $PaCO_2$. For example brain blood flow can be measured by various modalities that include trans-cranial Doppler, positron emission tomography (PET) and single proton emission tomography (SPECT), and nuclear magnetic resonance imaging (MRI) techniques such as blood oxygen level dependent (BOLD) and arterial spin labeling (ASL) echo. $CO_2$ is used as the provocative stimulus to induce a change in blood flow and thus measure the vascular reactivity. Traditional methods have assumed that infusing $CO_2$ into a mask will change the $PaCO_2$. Infusing the $CO_2$ into the mask changes the exhaled $PCO_2$ but this is unreliably related to the $PaCO_2$, the actual physiological stimulus at the site of action. It has been shown by Prisman et al[1]. and Hoskins et al.[2] that this is totally ineffective (see discussion in Prisman[1] and Mark et al.[3, 4]). Still, infusion of $CO_2$ into a mask or fixing the inspired $PCO_2$ is nevertheless still used for studying brain vascular reactivity. With this method, one can detect a change in brain blood flow but because one doesn't know the $PaCO_2$, the actual reactivity is unknown. For example, a small change in the measure of blood flow may be due to low reactivity or small change in $PaCO_2$.

An improved method of implementing changes in $PaCO_2$ has been presented by Prisman et al.[1]. The theory presented by Slessarev et al.[5] is that sequential gas delivery provides good reliability in targeting a change in $PaCO_2$. The theory of such targeting requires the delivery of a first gas which has a predetermined concentration of oxygen and $CO_2$ to affect a $PaCO_2$ at the first part of the breath and the remainder of the breath consists of a second gas which has $CO_2$ concentration equal to the target $PaCO_2$. Ito et al.[6] applied such a circuit to spontaneously breathing humans and found that targeting with this system the expired partial pressure of $CO_2$ was substantially equal to $PaCO_2$ within about 2 mmHg. This is sufficiently accurate for most, but not all purposes. For example, calibration of MRI BOLD signals to measure oxygen consumption of the brain require as accurate determination of $PaCO_2$ as can be obtained, and small discrepancies reduce the value of the calibration (Mark et al.). One source of error with the sequential gas delivery circuit is that some first gas continues to flow and be inhaled during the second gas delivery phase where it is desired that only second gas be inhaled. This is a limitation of all sequential gas delivery circuits. A variety of active or passive valves to prevent the first gas delivery during the phase where only second gas delivery is desired make the system more cumbersome, uncomfortable for the subject, and more expensive.

SUMMARY OF THE INVENTION

According to one aspect, the present invention is directed to a method of preparing a carbon dioxide ($CO_2$)-containing gas ($G_n$) that is organized for delivery in tandem with a second gas ($G_0$), in manner that composes a respiratory gas ($G_R$) and maintains a target $CO_2$ concentration ($FCO_2^T$) in a cumulative volume of the $G_R$ of interest ($CVG_R^T$), the method comprising:

for each successive time point of interest in a growing time period comprising all time points of current interest $T_1$ to $T_{last}$, each successive time point in turn a $T_{last}$:
  (a) obtaining input comprising or sufficient to compute:
    (i) a cumulative volume of $G_R$ ($CVG_R$) organized for delivery as of $T_{last}$ over all time points of current interest $T_1$ to $T_{last}$; and
    (ii) a cumulative volume of $CO_2$ ($CVCO_2$) organized to compose part of the $CVG_R$ as of $T_{last}$ in all time points of current interest $T_1$ to $T_{last}$;
  (b) using the input obtained to compute a respective incremental volume of $G_n$ that must be delivered as of $T_{last}$ so that the cumulative volume of $CO_2$ in the $CVG_R$ equals $FCO_2^T$; and
  (c) controlling a gas delivery means ($GD_n$) so that the respective incremental volume of $G_n$ targets $FCO_2^T$.

As of each successive time point of interest $T_{last}$ (for convenience also called $T_{current}$), in a time period of interest, the $CVG_R$ is understood to comprise all incremental volumes of $G_0$ organized for delivery as of $T_{last}$ (which cumulatively make up, as of each successive $T_{last}$, a new $CVG_0$ for the respective incremented time period of last interest comprising the time points $T_1$, to last $T_{last}$) and all incremental volumes of $G_n$ organized for delivery as of $T_{last}$ (which cumulatively make up, as of each successive $T_{last}$, a new $CVG_n$ for the respective incremented time period of last interest comprising the time points $T_1$ to last $T_{last}$). As described below, consonant with one suitable placement of the sensors used to track the actual incremental volumes of gas organized for delivery, input of $CVG_R$ for the last incremented time period may be simply obtained by adding the respective $CVG_n$ and $CVG_O$ values for this time period (sensor placement is organized to track incremental volumes of $G_O$ and $G_n$ as of each $T_{last}$ which are then incremented to obtain new values of $CVG_n$ and $CVG_O$ for each successive time point). Alternatively, input of the $CVG_R$ may be obtained by using a sensor to directly track incremental volumes of $G_R$ organized for delivery. As explained below, tracking respective $CVG_n$ and $CVG_O$ values for each $T_{last}$ may in some instances be sufficient to compute a respective incremental volume of $G_n$ that must be delivered as of $T_{last}$ so that the cumulative volume of $CO_2$ in the $CVG_R$ equals $FCO_2^T$ (e.g. without directly computing a respective $CVCO_2$ value for each time point of interest). Various embodiments of the invention described hereafter refer to obtaining input of alternative cumulative volume terms needed for computing a respective incremental volume of $G_n$ that must be delivered so that the cumulative volume of $CO_2$ in the $CVG_R$ equals $FCO_2^T$.

The expression "of interest" with reference to time points of interest, is to be understood to encompass time points that simply correspond to events that mark the beginning or end of a period of gas delivery (e.g. for a certain number of breaths, planned or arbitrarily terminated, or completion of a treatment or completion of a contemporaneous medical procedure or diagnostic test) but could also mean "directly" of interest insofar as the time span of making $G_R$ available for breathing begins and ends at specified points in time, whether predetermined or simply arbitrary. It will be appreciated that computation of an error signal and related control of a gas delivery device is done at selected time increments (e.g. every "x" milliseconds) which implies, that within a time span of interest, time points corresponding to those increments are inherently of interest. Since time points of interest are generally time points used to compute $e_n$, contiguous time points of interest are considered to be adjacent time points defining intervals of interest for computation of $e_n$. Similarly, a volume or cumulative volume of interest may be of interest simply in the sense that it defines one or a series of successive cumulated volumes that define reference volumes for calculation of an error signal.

By computing and controlling the delivery of an incremental corrective volume of $G_n$ that must be added to combined volume of the $CVG_n$ and $CVG_O$ (the $CVG_R$) to target the $FCO_2^T$ as of each successive time point $T_{last}$, the $G_n$ is understood to be functionally organized for delivery in tandem with the $G_O$.

In one preferred embodiment of the invention, each incremental volume of gas organized for delivery by a gas delivery means ($GD_n$) may be flowed to a patient, for example via an output port which leads unimpededly to a patient airway interface (e.g a mask) or a volume of gas that a patient is free or forced to intake (closely following release by the $GD_n$). In this connection, it is convenient to speak of incremental volumes, of defined magnitude determined by a sensor, 'delivered' (i.e. released for delivery) by a GDn (as well as incremented cumulative gas volumes based on these incremental volume values), as 'delivered' volumes. The phraseology 'actually delivered' may be also be used (with the same intended meaning) for emphasis.

The term "blending" may be used to describe the act of organizing delivery of $G_n$ in tandem with the $G_O$ and hence the term blending optionally encompasses physical blending and coordinated release of components of the $G_R$ to a patient.

According to another aspect, the present invention is directed to a method of using a respiratory gas delivery system having one or more gas output ports to coordinate the output of a carbon dioxide ($CO_2$)-containing gas ($G_n$) and a second gas ($G_O$), in a manner that composes a respiratory gas $G_R$, the method comprising:

for respective time points in a series of time points of interest:
  a) obtaining input of a cumulative volume of $G_O$ ($CVG_O$) or $G_R$ ($CVG_R$) delivered to a gas output port over a period comprising the series of time points of interest;
  b) obtaining input of a cumulative volume of $G_n$ ($CVG_n$) or $CO_2$ ($CVCO_2$) delivered to a gas output port over a period comprising the series of time points of interest;
  c) using the input obtained to compute an incremental volume of $G_n$ that must be delivered to an output port in tandem with the delivered $G_O$ so that the cumulative volume of $CO_2$ in a volume of the respiratory gas of interest ($CVG_R^I$) equals a target $CO_2$ concentration ($FCO_2^T$); and optionally
  d) controlling a gas delivery means ($GD_n$) so that respective incremental volumes of $G_n$ delivered to an output port target $FCO_2^T$.

The term "equals" as used herein preferably connotes mathematical equality but more broadly connotes a functional approximation of $FCO_2^T$ based on computation of a corrective volume of $CO_2$ in circumstances where such computation relies on inputs of incremented cumulative volumes $G_O$ and/or $G_R$ and $G_n$ and/or $CO_2$ i.e. such data is used as a basis upon which to compute, at respective time points of interest, a volumetric correction factor used to deliver an incremental amount of $G_n$ to adjust the cumulative amount of $G_n$ in a cumulative volume of $G_R$ of interest so that the cumulative amount of $CO_2$ is adjusted to at least functionally achieve a $FCO_2^T$. The term "target" in the same vein, broadly connotes the use any suitable control signal that implement the computation in step c) to deliver a corrective incremental volume of $G_n$.

The phrase "obtaining input" is meant to be broadly construed as encompassing any form of obtaining input that allows the input to be used. For example, a processor, optionally, in the form a microprocessor, may be programmed to receive a signal or data, for example a signal generated by a sensor or user input, or perform a computation using, for example, the aforementioned input, in order to generate the particular inputs required to compute an error signal, and ultimately, a control signal to a gas delivery device GDn.

Optionally, $CVG_R^I$ is equated to $CVG_R$. Optionally, $CVG_R^I$ consists of (is equated to) or comprises the $CVG_R$ for example the sum of $CVG_R$, and an incremental volume of $G_R$ that is designated to be delivered based on an adding a corrective incremental amount of $G_n$ to an incremental volume of $G_O$ predicted to be delivered to an output port in an ensuing time point for which sensor data is not available (optionally relying on actual data for relevant time points, optionally one more or more immediately preceding time points). The $CVG_R^I$ may consist of, comprise or otherwise takes into account the $CVG_R$ (as a base principle, taking $CVG_R$ into account enables computation of a corrective volume of $G_n$ based on volumes of gases actually made available for delivery). Therefore, $CVG_R^I$ is preferably a selected function of $CVG_R$, optionally a function which adds one or more defined incremental volumes to the $CVG_R$ as exemplified herein. The invention also contemplates a function in which a defined volume is subtracted from $CVG_R$, for example as another form of corrective measure, for example for adjusting the inspired "dose" of carbon dioxide.

Optionally, a $CVG_R$ is available for immediate inspiration (i.e. following commencement of $G_n$ delivery by $GD_n$ to an output port) and $FCO_2{}^T$ is attained within a cumulative $G_R$ inspiratory volume of no greater than 50 litres, optionally no greater than 10 litres, optionally no greater than 5 litres, optionally no greater than one liter optionally no greater than 500 ml, optionally within a cumulative $G_R$ inspiratory volume of no greater than 100 ml, optionally within a cumulative $G_R$ inspiratory volume of no greater than an average human adult or infant breath, optionally within a cumulative $G_R$ inspiratory volume of 25 mls, optionally within a time span of a single average inspiration, optionally within in a time span of 1 to 3 seconds. Optionally, the $FCO_2{}^T$ is continuously maintained after being after being attained.

The phrase "in tandem" means at least coordination in a volumetric sense to achieve proportioned output of $G_n$ that matches output of $G_0$. However, the output of the respective components of a respiratory gas $G_R$ in a respiratory gas delivery system may typically be needed or potentially needed in an immediate sense (in real time), for example, where the output flows in real time to a patient airway interface such as a mask or endotracheal tube or to one more gas reservoirs the contents of which may (either immediately, imminently or as needed) be drawn on or delivered breath by breath. The present invention notably enables such coordination to be scaled from both a time and volumetric standpoint to at least within a human (adult or infant) breath so that the volume of pure $CO_2$ in the $CVG_R{}^I$ (where $CVG_R{}^I$ is a breath or a partial breath of minimum size e.g. 10-25 ml., having regard to the volume/precision specifications of the $GD_n$ and other components) equals $FCO_2{}^T$.

The term output port with reference to delivery of $G_n$ broadly means any port or junction downstream of a gas delivery means ($GD_n$), through which the volumetric output of $G_n$ is controlled as described below so that actual respective volumes of $G_n$ delivered downstream of the $GD_n$ target $FCO_2{}^T$. Because incremented amounts of $G_0$ are directly or indirectly part of the input of a control system, optionally embodied in a computer, the incremental amounts $G_n$ for respective time points are effectively delivered in tandem with delivery of the $G_0$ (delivery may result in release of $G_0$ to a patient in real time or optionally take the form of volumetrically controlled accumulation of the $G_0$ e.g. if a combined gas or respective individual gases are accumulated for delivery). As described below the invention contemplates the use of a control system to set a target $FCO_2{}^T$, to obtain inputs of the requisite cumulative volumes of $G_0$ ($CVG_0$) or $G_R$ ($CVG_R$) over a period comprising the series of time points of interest, to obtain input of a cumulative volume of $G_n$ ($CVG_n$) or $CO_2$ ($CVCO_2$) over a period comprising the series of time points of interest, to compute an corrective amount incremental amount of $G_n$ needed to target $FCO_2{}^T$ ($e_n$) for those respective time points, to control the gas delivery means (e.g. a valve) in order to increment the delivered amount of $G_n$ so as to target $FCO_2{}^T$ and where required (e.g.) where the concentration of $CO_2$ in the $G_n$ and optionally $G_0$ is not fixed to receive input of sensors that detect concentration of gases and compute an $e_n$ accordingly. As described below this control system may be variously embodied in one or more hardware components in a manner well known in the art.

According to one embodiment of the invention, a respiratory gas delivery system may comprise a conventional ventilator, anesthetic machine or other respiratory gas delivery device (machine or manually operated) having an output port for the $G_0$ (leading, optionally unimpeded, to a $G_0$ containing reservoir or a patient airway interface) which is operatively coupled to a separate $G_n$ delivery device having an output port directly into the $G_0$ (for example into a $G_0$ delivery conduit) or into a common volume (e.g. a patient airway interface, reservoir, manifold, connector) or different volumes which are organized to be delivered proportionately for maintaining $FCO_2{}^T$ and preferably contemporaneously and in real time (i.e. resulting in the targeted concentration of $CO_2$ in a volume of the $G_R$ to be maintained (after an initial ramp up time) continuously. The cooperation among two devices having respective individual output ports or a common output port from the standpoint of eventual output to the patient may be understood to be a retrofit or of a priori design, The invention also contemplates a respiratory gas delivery system in the which a $G_0$ delivery system and $G_n$ delivery system are integrated in a common unit.

Optionally, as described below, at successive time points within a series of time points of interest, an error term as hereafter described, may be computed.

As elaborated below, a key nature of the respective time points of interest are those for which there are available inputs of incremented cumulative volumes $G_0$ and/or $G_R$ and $G_n$ and/or $CO_2$. These inputs may be derived from sensors that generate the signals required to obtain input of the incremented cumulative volumes of gases delivered to an output port. In this manner the requisite input is obtained for computing, at respective time points, an incremental volume of $G_n$ that must be delivered to an output port in tandem with the delivered $G_0$ so that the cumulative volume of $CO_2$ in the $CVG_R{}^I$ equals $FCO_2{}^T$. Accordingly, the series of time points of interest for which respective cumulative volumes of gases are obtained and computations of an error term, as described below, are made, are understood to minimally accord at least with a particular application for which the respiratory gas delivery system is used i.e. requisite degree of precision for proportionally matching $G_n$ and $G_0$ at least volumetrically and to match the requisite contemporaneous nature of the coordination in terms of ensuring the fraction and/or size and/or number of the breath(s) for which a $CO_2$ adjusted composition of a $CVG_R{}^I$ is sought to be achieved is timely attained and maintained. Accordingly, the respective time points of interest for which respective incremented volumetric inputs ($CVG_0$ and/or $CVG_R$ and $CVG_n$ and/or $CVCO_2$) to compute an error term is obtained, must at least closely correspond to one another and to the time points for which sensor data input is obtained.

Optionally, as described below, at successive time points within a series of time points of interest an error term may be computed. Optionally, this series of time points of interest may be described as the most current continuous period of interest for which the targeted $CO_2$ concentration in a cumulative volume of $G_R$ of interest is maintained. The invention contemplates that the actual delivery of this $CVG_R{}^I$ to the patient may lag in time. Therefore, $T_{current}$ is not necessarily a $T_{now}$ in the sense of according with a current device clock time/volume sensor reading. Nevertheless, each successive time point is preferably a time point of interest at least in the sense in which it corresponds to one of the respective time points for which incremented cumulative volumes required for computation of $e_n$ is used. Each respective time point in a series of interest can be understood to become, in turn, a current time point $T_{current}$ (optionally a $T_{now}$) at which the delivered volumes of $G_n$, $G_0$, and $CO_2$ are updated based on sensor readings and these updated values can be used at each respective time point of interest for computing an error term $e_n$. The error term $e_n$ is optionally equated to a volume of $G_n$ that must be delivered so that the volume of pure $CO_2$ in the combined volumes of $CVG_n$, $CVG_0$, and $e_n$ equals $FCO_2^T$. The error term is converted by a controller ($VC_n$) into a signal that is delivered to a $GD_n$ so that an incremental volume of $G_n$ is delivered by the $GD_n$ to target a $CO_2$-concentration of $FCO_2^T$ in the incremented volumes of $CVG_n$ and $CVG_0$. Optionally, the $VC_n$ takes the form of a PI controller. Optionally, the $VC_n$ takes the form of any controller known to those skilled in the art that can accept input of $e_n$ and compute a signal for $GD_n$ to deliver an incremental volume of $G_n$ to target $FCO_2^T$. The output to the $GD_n$ for a respective $T_{current}$ may be generated from a weighted sum of $e_n$ for the respective $T_{now}$, the integral of $e_n$ over a time period $T_1 \ldots T_{current}$, and the derivative of $e_n$ for the respective $T_{current}$.

According to another aspect, the present invention is directed to a device for coordinating the output of a carbon dioxide ($CO_2$)-containing gas ($G_n$) and a second gas ($G_0$), in a manner that composes a respiratory gas $G_R$, the device comprising:
  a) a control system for delivery of incremental amounts of $G_n$ in tandem with the $G_0$ at successive time points in a series of time points of interest, wherein the respective incremental amounts of $G_n$ are selected to attain a target $CO_2$ concentration ($FCO_2^T$) in a cumulative volume of the $G_R$ ($CVG_R$); and
  b) a gas delivery means ($GD_n$) for delivering the respective incremental volumes of $G_n$ to a $G_n$ channeling means;
the control system comprising means for obtaining input of a cumulative volume of $G_0$ ($CVG_0$) or $G_R$ ($CVG_R$) delivered to a $G_0$ channeling means; means for obtaining input of a cumulative volume of $G_n$, ($CVG_n$) or $CO_2$ ($CVCO_2$) delivered by the $GD_n$ over a period comprising the series of time points of interest, means for using the input obtained to compute an incremental volume of $G_n$ that must be delivered to the $G_n$ channeling means in tandem with the $G_0$ so that the cumulative volume of $CO_2$ in $CVG_R$ equals $FCO_2^T$; and means for controlling the $GD_n$ so that respective incremental volumes of $G_n$ delivered to the $G_n$ channeling means target $FCO_2^T$. Optionally, the device comprises a volume sensor for obtaining input of a cumulative volume of $G_n$ ($CVG_n$) or $CO_2$ ($CVCO_2$) delivered by the $GD_n$. Optionally, the device comprises input means for setting the $FCO_2^T$. Optionally, the control system is implemented by a processor in the form of a computer as broadly defined herein. The processor is optionally embodied in an IC chip. The term "configured" when used in relation to a computer is non-limiting in the sense that any one or more its functions may be accomplished by a computer program product or via a memory of any type or hard-wired into a dedicated circuit or implemented via electronic components (consonant with the broadest definition of the term computer used herein).

The present invention is directed to a method of delivering to a subject a carbon dioxide ($CO_2$)-containing gas ($G_n$) and a second gas ($G_0$), in a manner that composes a respiratory gas $G_R$, the method comprising:
for respective time points in a series of time points of interest:
  a) obtaining input of a cumulative volume of $G_0$ ($CVG_0$) or $G_R$ ($CVG_R$) delivered to a subject over a period comprising the series of time points of interest;
  b) obtaining input of a cumulative volume of $G_n$ ($CVG_n$) or $CO_2$ ($CVCO_2$) delivered to a subject over a period comprising the series of time points of interest;
  c) using the input obtained to compute an incremental volume of $G_n$ that must be delivered to the subject in tandem with the delivered $G_0$ so that the cumulative volume of $CO_2$ in a volume of the respiratory gas of interest ($CVG_R^I$) equals a target $CO_2$ concentration ($FCO_2^T$); and optionally
  d) controlling a gas delivery means ($GD_n$) so that respective incremental volumes of $G_n$ delivered to the subject target $FCO_2^T$.

The present invention is also directed to a method of blending a carbon dioxide ($CO_2$)-containing gas ($G_n$) and a second gas ($G_0$), in a manner that composes a respiratory gas $G_R$ for delivery to a subject, the method comprising:
for respective time points in a series of time points of interest:
  a) obtaining input of a cumulative volume of $G_0$ ($CVG_0$) or $G_R$ ($CVG_R$) designated for delivery to a subject over a period comprising the series of time points of interest;
  b) obtaining input of a cumulative volume of $G_n$ ($CVG_n$) or $CO_2$ ($CVCO_2$) designated for delivery to a subject over a period comprising the series of time points of interest;
  c) using the input obtained to compute an incremental volume of $G_n$ that must be designated for delivery to a subject in tandem with the delivered $G_0$ so that the cumulative volume of $CO_2$ in a volume of the respiratory gas of interest ($CVG_R^I$) equals a target $CO_2$ concentration ($FCO_2^I$); and
  d) optionally controlling a gas delivery means ($GD_n$) so that respective incremental volumes of $G_n$ delivered to the subject target $FCO_2^T$.

In another aspect, the present invention is also directed to an integrated circuit (IC) chip configured for carrying out a method as described herein.

In another aspect, the present invention is also directed to a computer program product comprising a non-transitory computer readable medium encoded with program code for controlling operation of an electronic device, the program code including code for computing an error term $e_n$ corresponding to the incremental volume of $G_n$ computed for the respective time points of interest. Optionally, the program code includes code for computing or obtaining input of a set of parameters comprising $CVG_R$ and $CVCO_2$. Optionally, the program code includes code for controlling a gas delivery means ($GD_n$) so that respective delivered incremental volumes of $G_n$ target $FCO_2^T$.

In another aspect, the present invention is also directed to device comprising an integrated circuit chip configured for carrying out the method, for example a printed circuit board (comprising discrete electronic components). The device optionally includes at least one gas delivery means and optionally at least one volume sensor as hereinafter defined. The device optionally includes an input device for inputting $FCO_2^T$. Optionally, $FCO_2^T$ can be input via a variety of means including, but not limited to, a keyboard, mouse, dial, knob, touch screen, button, or set of buttons. Optionally, the target $FCO_2^T$ can be changed at any time.

The device optionally includes at least one $CO_2$ containing gas delivery conduit.

In one embodiment, the present invention is directed to a method for adding at least one carbon dioxide-containing gas ($G_n$) to an inspiratory gas ($G_0$), to formulate a respiratory gas ($G_R$) for delivery to a subject, and to maintain a targeted concentration of carbon dioxide ($FCO_2^T$) in a volume of the $G_R$ of interest ($CVG_R^I$), comprising:
for each of a group of respective time points of interest comprising
  $T_1 \ldots T_{current}$, each in turn a respective $T_{current}$:

(A) obtaining input of a cumulative volume of $G_n$ ($CVG_n$) or $CO_2$ ($CVCO_2$) actually delivered over all time points $T_1 \ldots T_{current}$;
(B) obtaining input of a cumulative volume of $G_0$ ($CVG_0$) or $G_R$ ($CVG_R$) actually delivered over all time points $T_1 \ldots T_{current}$;
(C) computing the incremental volume of $G_n$ that must be delivered to the subject so that the cumulative volume of $CO_2$ in the $CVG_R^I$ equals $FCO_2^T$;
(D) controlling a gas delivery means ($GD_n$) so that the delivered incremental volume of $G_n$ targets $FCO_2^T$.

In one embodiment, an error term ($e_n$) is computed that represents the incremental volume of $G_n$ that must be delivered to the subject so that the cumulative volume of $CO_2$ in the $CVG_R^I$ (e.g. the actual $CVG_R$) equals $FCO_2^T$.

Therefore, according to one embodiment, the invention is directed to a method of adding at least one carbon dioxide ($CO_2$) containing gas ($G_n$) to an inspiratory gas $G_0$, to formulate a respiratory gas ($G_R$) for delivery to a subject, and to maintain a targeted concentration of $CO_2$ in a volume of the $G_R$, comprising:
for each of a group of respective time points of interest $T_1 \ldots T_{current}$ each in turn a respective $T_{current}$:
(A) obtaining input of a cumulative volume of $CO_2$ ($CVCO_2$) actually delivered (optionally determined, based on sensor readings, as a volume of $CO_2$ incremented at successive respective time points $T_1 \ldots T_{current}$);
(B) obtaining input of a cumulative volume of $G_0$ ($CVG_0$) or $G_R$ ($CVG_R$) actually delivered (optionally determined, based on sensor readings, as volumes of $G_0$ or $G_R$ incremented at successive respective time points $T_1 \ldots T_{current}$);
(C) based on an ascertained concentration of $CO_2$ in $G_n$, computing an error term ($e_n$) equal to the volume of $G_n$ that must be delivered so that the cumulative volume of $CO_2$ in $CVG_R$ equals a desired fraction $FCO_2^T$;
(D) controlling a gas delivery means $GD_n$ so that the actual incremental volume of $CO_2$ delivered as part of the $CVG_R$ targets $FCO_2^T$.

In one embodiment, a suitable controller (e.g. a PI or PID controller) is used to control the gas delivery means ($GD_n$) so that the delivered incremental volume of $G_n$ targets $FCO_2^T$.

The term "fraction" and "concentration" are generally used interchangeably herein based on the understanding that a particular choice of algorithm and units (if any) for expressing concentration may vary based on whether partial pressures, fractional concentrations or percentages are used for expressing a target concentration of $CO_2$ in a volume of $G_R$. The abbreviations $FCO_2^T$ and $CO_2^T$ are also used interchangeably.

The term "respiratory gas" means a group of at two component gases that are suitable for inhalation by a subject individually or at least when combined and that meet a criterion with respect the concentration of carbon dioxide in any combined volume of the group of component gases. Accordingly, in a clinical setting where any particular combined volume of the component gases is inhaled over a particular time period by a subject, as a single stream of combined component gases or multiple streams in parallel, the $FCO_2^T$ with respect to a cumulative volume of $G_R$ inhaled by the subject over a period of interest (e.g. a single breath) will have been maintained.

The actual cumulative volume of $G_R$ (referred to as $CVG_R$) is understood to include, as preferred, the incremental volume of $G_n$ that must be delivered to the subject so that the cumulative volume of $CO_2$ in the $CVG_R^I$ equals $FCO_2^T$.

As described above, in one embodiment of the invention the $CVG_R^I$ is equated to the $CVG_R$. In one embodiment of the invention described below, at a respective $T_{current}$, an assumption is made about how much inspiratory gas $G_0$ (the $G_0$ is alternately referred to as a second gas, the $G_n$ alternately being referred to as a first gas) will be delivered between $T_{current}$ and an ensuing time point. Accordingly, in addition to computing the incremental volume of $G_n$ that must be delivered so that the cumulative volume of $CO_2$ in the $CVG_R$ equals $FCO_2^T$ it may expedient to compute at $T_{current}$, the $G_n$ that would be need to be delivered to target the $FCO_2^T$ within a particular assumed incremental amount of $G_0$.

In the latter connection, $CVG_R^I$ may optionally be computed as the sum of the $CVG_R$, the assumed incremental volume of $G_0$ and the incremental volume of $G_n$ that would be sought to be delivered to target the $FCO_2^T$ within that incremental amount of $G_0$. The computation of $CVG_R^I$ may serve other purposes as well and hence computation of $CVG_R^I$ (however approached) is understood to preferably be a function of an actual $CVG_R$ value, for a respective $T_{current}$, whereby one can consequently compute the incremental volume of $G_n$ that must be delivered so that the cumulative volume of $CO_2$ in a particular cumulative volume of $G_R$ (i.e. taking into account a $CVG_R$ value) equals $FCO_2^T$.

Obtaining input of $CVG_n$ is expressed as an alternative to obtaining input of $CVCO_2$. In most cases, using $CVCO_2$ as an input for computation of $e_n$ will be preferable (optionally as an incremented volume of $CO_2$, incremented at each successive $T_{current}$ within a series of time points of interest) as this approach best serves (in the broadest range of circumstances) the computational purpose of continuously tracking the incremental volume of pure $CO_2$ that must be delivered to target $FCO_2^T$ having regard to the incremented cumulative volume of pure $CO_2$ contributing to the incremented cumulative volume of $G_R$. Obtaining input of $CVG_n$ incidental to the goal of computing the error term $e_n$ may be understood to be practical as an input parameter, in a physical sense (from volume sensor readings), and beyond that tracking $CVG_n$ computationally may in theory be adequate (e.g where the $G_0$ is devoid of $CO_2$ and the concentration of $CO_2$ in $G_n$ is fixed) as a surrogate method of tracking $CVCO_2$. However, in most instances, using $CVG_n$ as a plausible alternative input parameter for computing the error term $e_n$ (e.g. especially where it must be matched with a changing value of a variable concentration of $CO_2$ in $G_n$—and optionally also a fixed or changing value of a variable concentration of $CO_2$ in $G_0$—applicable to each respective $T_{current}$) may be computationally unwieldy. Therefore, optionally, determining a cumulative volume of pure $CO_2$ ($CVCO_2$) delivered in a particular time interval, for example, a period of interest $T_1$-$T_{current}$, may serve the purpose of computing $e_n$ most universally and efficiently by accommodating input of a value for the concentration of $CO_2$ in $G_n$ (this value may 100% or less than 100%) and a value for the concentration of $CO_2$ in $G_0$ (as this value may be 0% or more than 0%). This may be done by incrementing the volume of $CO_2$ from the last $T_{current}$ by the incremental volume of $G_0$ and $G_n$ delivered since the last $T_{current}$ weighted by their concentrations of $CO_2$. Therefore it will be appreciated that even though obtaining input of both $CVCO_2$ and $CVG_R$ for each respective time of interest is the most universally pragmatic way of computing the corrective volume of $G_n$ that must be added to the cumulative volume of $G_R$ as of each time point of interest, in some instances, as explained above, the input sufficient to compute this corrective volume may be geared to alternative mathematically equivalent terms and algorithms. Hence, it will be appreciated that certain alternative combinations of inputs are to be viewed as particular embodiments falling within a broader range of alternatives, namely inputs sufficient to compute $CVCO_2$ and $CVG_R$ (i.e. algorithms using surrogate cumulative volume terms and any other input values such as $CO_2$ concentrations in $G_n$ and $G_0$ would invariably use a combination of inputs sufficient to compute both $CVCO_2$ (a cumulative volume of the pure component of interest) and $CVG_R$)

As elaborated below, each successive time point within a period of interest becomes a current time point $T_{current}$ at which the cumulative volumes of pure $CO_2$ and/or $G_n$ and, $G_0$ and/or $G_R$, are updated based on sensor readings (which may output actual incremental volumes of the respective gases at each respective $T_{current}$) and these updated values can be used for computing the error term $e_n$. The error term is a volume of $G_n$ computed at successive time points $T_{current}$ that is converted by a controller into a signal delivered to the $GD_n$ to target (having regard to the limitations of the hardware) the desired concentration of carbon dioxide that is input or preset ($CO_2^T$). Thus the $GD_n$ is signaled to deliver a corrective volume of gas. Expressed in terms of time points identified herein, the corrective volume may optionally be considered to be delivered during the time interval beginning at the respective $T_{current}$ and optionally ending at $T_{current+}$, optionally the immediately next ensuing $T_{current+1}$. The term "gas delivery means", abbreviated $GD_n$ and alternatively to as a "gas delivery device" refers to specifically to hardware for delivering (e.g. releasing, where the source gas is under pressure) specific volumes of $G_n$ into the respiratory gas inspired by the patient, preferably a device that is adapted to introduce volumes of variable incremental size into the respiratory gas, for example directly into a $G_n$ carrying conduit, optionally into an inert conduit (inert vis-à-vis the composition of the $G_n$), optionally a conduit that feeds directly into a conduit carrying the $G_0$ stream such as an inspiratory limb of a breathing circuit. The gas delivery means may be any known gas delivery device such as a gas injector, or a valve, for example, a proportional flow control valve.

The term "pure $CO_2$" is used broadly to facilitate defining a fraction of a volume of delivered $CO_2$ containing gas (theoretically pure $CO_2$) that allows one to compute $e_n$ and/or other parameters described herein Optionally, in one embodiment of the invention, the output to the $GD_n$ for a respective $T_{current}$ is generated from a weighted sum of $e_n$ for the respective $T_{current}$ and the integral of $e_n$ for the respective $T_{current}$ (e.g. based on a signal from a PI controller). Optionally, the gas delivery means $GD_n$ is controlled using a controller ($VC_n$) in the form of a PID controller. Optionally, the group of respective time points of interest defined with respect to the respective $T_{current}$ define a cumulative time period ($T_{variable}$) beginning at a resetable $T_{start}$ and ending at an incrementally advancing time point ($T_{end}$) equated to the respective $T_{current}$ and the signal to the $GD_n$ applicable to a respective $T_{current}$ is computed using only an actual $CVG_n$ and/or $CVCO_2$, and $CVG_0$ and/or $CVG_R$ delivered in the time period $T_{variable}$. In another embodiment of the method, the group of respective time points of interest defined with respect to the respective $T_{current}$ define a cumulative time period ($T_{variable}$) beginning at a resetable $T_{start}$ and ending at a an incrementally advancing time point ($T_{end}$) equated to the respective $T_{current}$ and the signal to the $GD_n$ for a $T_{variable}$ corresponding to a respective $T_{current}$ is computed based on:

(a) the output of the controller; and
(b) an incremental volume of $G_0$ presumed to be delivered in the time interval $\Delta T$ between the respective $T_{current}$ and a ensuing time point $T_{current+}$ ($G_0^P$). Accordingly, based on a predicted concentration of $CO_2$ in $G_0^P$ ($FCO_{20}^P$) the signal to the $GD_n$ may also deliver an incremental volume of $G_n$ that must be added to $G_0^P$ ($G_n^P$) so that the incremental volume of $CO_2$ in the combined volume of $G_0^P$ and $G_n^P$ equals $FCO_2^T$.

A variety of different strategies could be used to add a predictive element to the aforementioned approach of keeping the delivered $G_n$ in step with the amounts of $G_0$ delivered so that the $e_n$ is lessened or less variable. According to one embodiment herein, the signal delivered to the $GD_n$ is computed based on the sum of the output of the controller $VC_n$ and a volume of $G_n$ that must be added to $G_0^P$ ($G_n^P$) so that the incremental volume of $CO_2$ in the combined volume of $G_0^P$ and $G_n^P$ equals $FCO_2^T$. A variety of alternative methods could be used to compute $G_0^P$ and $FCO_{20}^P$. Optionally, $G_0^P$ for the time interval $\Delta T$ corresponding to a respective $T_{current}$ is equated with a pre-defined value, an incremental volume of $G_0$ delivered during a previous time interval of interest, or with an average or weighted average of the volumes of $G_0$ delivered in a plurality of previous time intervals of interest. Optionally, $FCO_{20}^P$ can be equated with a pre-defined value, a concentration of $CO_2$ in the $G_0$ at a previous time point of interest, or with an average or weighted average of the concentration of $CO_2$ in the $G_0$ at a plurality of previous time points of interest. In general, $G_0^P$ and $FCO_{20}^P$ can be computed based on any combination of past data including, but not limited to, incremental volumes of $G_0$ delivered or the concentration of $CO_2$ in $G_0$, and/or the rate of change of $G_0$ delivery or the rate of change of the concentration of $CO_2$ in $G_0$, at one or a plurality of time points or time intervals of interest. Methods for computing $G_0^P$ and $FCO_{20}^P$ based on past data include, but are not limited to, averages, weighted averages, artificial intelligence, pattern recognition, rule definitions, look-up-tables, empirical formulas, or heuristics.

Optionally, the $T_{variable}$ corresponding to a respective $T_{current}$ is selectable based on a volumetric dimension of $CVG_0$ or $CVG_R$ of interest, or a volumetric dimension of $CVCO_2$ or $CVG_n$ of interest, a set of time points defined by an external event or a set of time points corresponding to a part of an inspiratory cycle, a full inspiratory cycle or a series of, parts of or full, inspiratory cycles. For example, the device of the present invention may be used to simulate sequential delivery of a pre-defined volume of $G_0$ delivered in the first part of any inspiratory cycle and a gas having a $CO_2$ content approximating the subject's arterial $PCO_2$ for the remainder of any inspiratory cycle.

As described above, in one embodiment, the $GD_n$ is a proportional flow control valve. The invention also encompasses intermittently turning on and off a two way solenoid, etc.

Optionally, the cumulative volume of $G_n$ ($CVG_n$) actually delivered at respective points $T_1 \ldots T_{current}$ is obtained via a "volume sensor" ($VS_n$) which can be constituted by any hardware for directly or indirectly measure a volume of $G_n$ e.g. an incremental volume of $G_n$, for example, a spirometer, a flow meter (by computing the integral of the flow), a CO2 analyzer which can be used, for example, to deduce the flow of $G_n$ which is then integrated to arrive at a volume etc. Input of a cumulative volume of $G_0$ ($CVG_0$) or $G_R$ ($CVG_R$) actually delivered over all time points $T_1 \ldots T_{current}$ may can be implemented by employing the output a second volume sensing means (a $VS_O$ or $VS_R$) depending on whether the volume of $G_0$ ($VS_O$) or the total volume of respiratory gas ($VS_R$) is being measured and/or computed.

The term "ascertained" when referring to a concentration of $CO_2$ in $G_n$ or $G_0$ applicable to any respective $T_{current}$ (or in an analogous context) is used to broadly refer to a variety of instances e.g. where a value is determined for a respective $T_{current}$ by a gas analyzer; where the need for ascertaining the $CO_2$ concentration is obviated by the algorithm (e.g. the fractional concentration of $CO_2$ is not directly taken into account as an input, for example, where the device is particularly to adapted to a $G_n$ consisting entirely of $CO_2$ or $G_0$ with 0% $CO_2$); where the concentration of $CO_2$ in the added gas is a fixed value based on a known concentration of $CO_2$ in the $CO_2$ containing source gas $G_n$ (e.g. an inputable preset concentration such as 90% or 100% $CO_2$) or where the concentration of $CO_2$ in the $G_0$ is a fixed value based on a known concentration of $CO_2$ in the $G_0$ (e.g. 0% $CO_2$ in air).

Optionally, the function of the controller $VC_n$ is carried out by a microcontroller which optionally also receives and/or computes the various inputs described above including one or more of the following: for each of a group of respective time points of interest $T_1 \ldots T_{current}$: $FCO_2^T$, $CVG_n$, $CVG_O$ and/or $CVG_R$, an error signal ($e_n$) equal to the volume of $G_n$ that must be delivered to the subject with the $G_0$ so that the cumulative volume of $CO_2$ in $CVG_R$ equals a desired fraction $FCO_2^T$; the output(s) of a volume sensing means ($VS_n$ and/or $VS_O$ and/or $VS_R$) and optionally, the output of a gas analyzer. Optionally, the inputs and computations are carried out by a general purpose microprocessor or CPU.

In one aspect, the invention is directed to a computer program product comprising a computer readable medium (non-transitory) encoded with program code for controlling operation of a device, the program code including program code for obtaining input of or computing, for each of a group of respective time points of interest $T_1 \ldots T_{current}$, each in turn a respective $T_{current}$, a set of parameters for computing an error signal ($e_n$) equal to an incremental volume of a $CO_2$ containing $G_n$ that must be delivered in step with a $G_0$ so that the cumulative volume of $CO_2$ in $CVG_R$ is maintained at a desired fraction $FCO_2^T$. In one embodiment, the set of parameter includes a respective $CVCO_2$ and $CVG_R$ for each respective $T_{current}$. In one embodiment, the program code comprises program code for controlling a gas delivery means ($GD_n$). In one embodiment, the program code generates a suitable signal corresponding to an actual incremental volume of $CO_2$ needed to targets $FCO_2^T$ for each respective $T_{current}$ within the group of respective time points of interest $T_1 \ldots T_{current}$. Any suitable method of control known to those skilled in the art, for example, a form of PI or PID control may be included in the program code.

It is understood that any input, computation, output, etc described herein can be accomplished by a variety of signal processing means including, but not limited to, a programmable processor, a programmable microcontroller, a dedicated integrated circuit, a programmable integrated circuit, discrete analog or digital circuitry, mechanical components, optical components, or electrical components. For example, the signal processing steps needed for executing the inputs, computations and outputs can physically embodied in a field programmable gate array or an application specific integrated circuit.

In another one aspect, the present invention is directed to a control system for a respiratory gas delivery system that controls the coordinated output of a carbon dioxide ($CO_2$)-containing gas ($G_n$) and a second gas ($G_0$), in a manner that composes a respiratory gas $G_R$, the control system comprising:

for respective time points in a series of time points of interest:
 a) means for obtaining input of a cumulative volume of $G_O$ ($CVG_O$) or $G_R$ ($CVG_R$) delivered over a period comprising the series of time points of interest;
 b) means for obtaining input of a cumulative volume of $G_n$ ($CVG_n$) or $CO_2$ ($CVCO_2$) delivered over a period comprising the series of time points of interest;
 c) means for using the input obtained to compute an incremental volume of $G_n$ that must be delivered so that the cumulative volume of $CO_2$ in a volume of the respiratory gas of interest ($CVG_R^T$) equals a target $CO_2$ concentration ($FCO_2^T$); and optionally
 d) means for controlling a gas delivery means ($GD_n$) so that respective incremental volumes of $G_n$ delivered target $FCO_2^T$.

Optionally, the control system includes means to obtain input of a $FCO_2^T$ It is understood that the control system is used to deliver the respective components of the $G_R$ in a manner that enables the requisite volumes to be tracked, whether the delivery is to an area of common volume or separate volumes organized to be delivered coordinately. Optionally, the control system is embodied in a computer as broadly defined herein.

In one aspect, the present invention is directed to a computer readable memory having recorded thereon computer executable instructions for carrying out one or more embodiments of the above-identified method. The invention is not limited by a particular physical memory format on which such instructions are recorded for access by a computer. Non-volatile memory exists in a number of physical forms including non-erasable and erasable types. Hard drives, DVDs/CDs and various types of flash memory may be mentioned. The invention, in one broad aspect, is directed to a non-transitory computer readable medium comprising computer executable instructions for carrying out one or more embodiments of the above-identified method.

In one embodiment, the invention is directed to IC chip designed to implement a method according to the invention. In one embodiment, the invention is directed to a printed circuits board comprising one or more hardware components for the implementing a control system as described above, for example an IC chip, adapted to implement a method according to the invention.

Optionally, the computer readable memory includes machine readable code to receive input of or compute for each of a group of respective time points of interest $T_1 \ldots T_{current}$) each in turn a respective $T_{current}$:
 (A) a cumulative volume of $G_n$ ($CVG_n$) actually delivered at all time points $T_1 \ldots T_{current}$, (optionally an incremental volume of $G_n$ delivered at each respective time point $T_{current}$ for computing $CVG_n$) or preferably a cumulative volume of $CO_2$ ($CVCO_2$) actually delivered as of all time points $T_1 \ldots T_{current}$, (optionally an incremented volume of $CO_2$ updated at each respective time point $T_{current}$ within a series of time points of interest);
 (B) a cumulative volume of $G_O$ ($CVG_O$) or $G_R$ ($CVG_R$) actually delivered at all time points $T_1 \ldots T_{current}$ (optionally an incremented volume of $G_O$ or $G_R$ delivered at each respective time point $T_{current}$ for computing $CVG_O$ and/or $CVG_R$);

(C) in accordance with a concentration of carbon dioxide ($CO_2$) in $G_n$ and $G_0$ applicable to the respective $T_{current}$, an error signal ($e_n$) equal to the volume of $G_n$ that must be delivered in step with the $G_0$ so that the cumulative volume of $CO_2$ in $CVG_R$ equals a desired fraction $FCO_2^T$.

The computer readable memory may also include machine readable code for controlling a gas delivery means ($GD_n$) so that the actual incremental volume of $CO_2$ coordinately delivered with $CVG_0$ (as part of $CVG_R$) targets $FCO_2^T$ (for example, any suitable controller known to those skilled in the art, for example, a PI or PID controller).

In another aspect, the present invention is directed to a device (an IC chip), CPU or microcontroller programmed to implement one or more embodiments of the above method. The program may include machine readable code as defined above. The program may be recorded on an integrated or external computer readable memory.

The aforesaid device may optionally include the following: the $VC_n$ and optionally, one or more components which serve one or more functions of: a $VS_n$, $GD_n$ and optionally a $G_n$ gas channeling means for example a port or $G_n$ gas delivery conduit for receiving the $G_n$ delivered by the $GD_n$.

Accordingly, according to another aspect, the invention is directed to a device for adding at least one added gas ($G_n$) to an inspiratory gas $G_0$, to formulate a respiratory gas ($G_R$) for delivery to a subject, and maintaining a targeted concentration of $CO_2$ in the $G_R$, comprising: a processing unit programmed to implement the method defined hereinabove (optionally, a CPU, microprocessor or microcontroller or dedicated circuit) and optionally, the $VC_n$ and optionally, the $VS_n$, $GD_n$ and a $G_n$ gas channeling means, for example a $G_n$ gas delivery conduit, for channeling the $G_n$ output by the $GD_n$.

The $G_n$ gas channeling means, optionally in the form of $G_n$ delivery conduit is optionally adapted to be operatively associated with or directly fluidically connected to a $G_0$ or $G_R$ gas channeling means, for example a $G_0$ or $G_R$ delivery conduit (e.g. an inspiratory limb of a breathing circuit) or any other gas channeling means e.g. a dedicated limb of a breathing circuit, a patient airway interface, a manifold, for example, a manifold for receiving multiple added gases or a connector interconnecting one or more of the above. Optionally, the device also includes a volume sensor ($VS_0$) operatively associated with the device for determining a cumulative volume of $G_0$ (or a volume sensor ($VS_R$) operatively associated with the device for determining a cumulative volume of inspired respiratory gas). The device optionally includes a $G_0$ channeling means e.g. a $G_0$ delivery conduit for delivering an inspiratory gas ($G_0$) to a subject. The term "delivery" to describe a conduit is used to in the sense of "channel" and does not imply the capacity to move a gas without a $GD_n$. Similarly, the termed "delivered" in the context of outcome of channeling a gas does not imply the capacity to move the gas into the patient's lung, but simply releasing a certain volume of gas to be available for spontaneous inhalation or to be moved by a ventilator.

In another aspect, the invention is directed to a respiratory gas delivery system for delivering a respiratory gas to a subject including a $G_0$ delivery system, for example a breathing circuit, a ventilator (manual or mechanical), an anesthetic machine etc.) and a $G_n$ delivery system incorporating one or more the features of a device or method as defined herein.

Accordingly in another aspect the invention is directed to a system for adding a carbon dioxide containing gas $G_n$ to an inspiratory gas ($G_0$) stream, to formulate a respiratory gas $G_R$, comprising:

(1) A first gas channeling means (optionally a first gas delivery conduit) for channeling an inspiratory gas ($G_0$) to a subject;

(2) A volume sensing means ($VS_0$) operatively associated with the system for determining a cumulative volume of $G_0$ ($CVG_0$) (or a volume sensing means ($VS_R$) operatively associated with the system for determining a cumulative volume of inspired respiratory gas ($CVG_R$));

(3) A $G_n$ delivery system for maintaining a targeted concentration of carbon dioxide ($CO_2$) in a cumulative inspired volume of the respiratory gas, including:

(A) a second gas channeling means (optionally a second gas delivery conduit) operatively associated with the first gas channeling means for channeling to the subject, coordinately with the $G_0$, a controlled volume of $G_n$;

(B) gas delivery means ($GD_n$) for releasing a variable incremental volume of $G_n$ into the second gas channeling means;

(C) a volume sensing means ($VS_n$) operatively associated with the device for determining a cumulative volume ($CVG_n$) of $G_n$;

(D) at least one computer (for example a dedicated circuit or CPU programmed to process machine readable instructions) for:

a) receiving input of:

(A) a target concentration of $CO_2$ ($FCO_2^T$) in any cumulative volume of inspired respiratory gas;

(B) the concentration of $CO_2$ in $G_n$ and $G_0$ as applicable;

(C) the output of a $VS_0$ and/or $VS_R$;

(D) the output of a $VS_n$;

b) computing for each of a group of respective time points of interest $T_1 \ldots T_{current}$, each in turn a respective $T_{current}$:

(A) a cumulative volume of $G_n$ ($CVG_n$) or pure $CO_2$ actually delivered as of all time points $T_1 \ldots T_{current}$;

(B) a cumulative volume of $G_0$ ($CVG_0$) or $G_R$ ($CVG_R$) actually delivered in as of all time points $T_1 \ldots T_{current}$;

(C) with respect to the concentration of $CO_2$ in $G_n$, an error signal ($e_n$) equal to the volume of $G_n$ that must be delivered to the subject with the $G_0$ so that the cumulative volume of $CO_2$ in $CVG_R$ equals a desired $FCO_2^T$;

c) for each respective $T_{current}$, controlling the gas delivery means $GD_n$ so that the actual incremental volume of $CO_2$ delivered to the subject in relation to $CVG_0$ or $CVG_R$ targets $FCO_2^T$.

The term computer is used broadly to refer to any device (constituted by one or any suitable combination of components) which may used in conjunction with discrete electronic components to perform the functions contemplated herein, including computing and obtaining input signals and providing output signals, and optionally storing data for computation, for example inputs/outputs to and from electronic components and application specific device components as contemplated herein. As contemplated herein a signal processor, processor or processing device (these terms used broadly and interchangeably unless a narrower meaning is implicit and means a CPU or computer in any suitable form) e.g. in the form of a computer may use machine readable instructions or dedicated circuits to perform the functions contemplated herein including without limitation by way of digital and/or analog signal processing capabilities, for example a CPU, for example a dedicated microprocessor embodied in an IC chip which may be integrated with other components, for example in the form of a microcontroller. Key inputs may include input signals from—a volume sensor such as a flow meter, a gas analyzer, any type of input device for inputting a $CO_2^T$ (for example, a knob, dial, keyboard, keypad, mouse, touch screen etc.) input from a computer readable memory etc. Key outputs include output of a control signal to control to a $GD_n$, including any control signal from a $VC_n$ based on an $e_n$ to target $CO_2^T$, for example PI control or PID control, an output signal to an alarm generating device etc. A variety of alternative forms of suitable control signals for controlling $GD_n$ are well known to those skilled in the art.

In one aspect, a $G_n$ delivery system according to the invention is part of a larger respiratory gas delivery system including a $G_0$ channeling means (for example a port or conduit for conducting the $G_0$, for example, forming part a manifold and/or one or more parts of a breathing circuit e.g. an inspiratory limb of a breathing circuit) and a volume sensor for obtaining input to determine a cumulative amount or $G_0$ or $G_R$ delivered. Optionally, a $G_n$ delivery system is an adjunct device which includes $G_n$ delivery components but does not include one or both of the first gas channeling means (e.g. a conduit or dedicated port) for delivering an inspiratory gas ($G_0$) to a subject or a volume sensor. The invention contemplates that a device according to the invention may nevertheless receive output from a volume sensor ($VS_0$) which is operatively associated with the device for determining a cumulative volume of inspired $G_0$ (or an equivalent volume sensor ($VS_R$) operatively associated with the device for determining a cumulative volume of delivered respiratory gas). The $G_n$ channeling means e.g. a port in a manifold or a delivery conduit (alternatively called an "added gas delivery conduit") may be readily adapted to be operatively associated with (e.g. connected to—the first gas delivery conduit or an airway interface (e.g. a mask, endotracheal tube etc. that interfaces with the subject's airway) in a manner suitable for channeling $G_n$ to the subject in tandem with the $G_0$. The device computer may be programmed to receive inputs of the $VS_0$. or $VS_R$ optionally in the form of a computed cumulative volume for use according to the invention or directly in the form of incremental volumes from which the device computer computes the requisite cumulative volumes.

The term "operatively associated" is generally (unless the context dictates otherwise) used expansively to mean "functionally associated", whether directly or indirectly, for a specified or implicit purpose. For example, a sensor will be operatively associated with the first gas ($G_0$) delivery conduit if it directly measures the volume of gas moving through the conduit at a selected time point or indirectly measures the volume of gas by measuring the combined volume of the $G_n$ and $G_0$ moving into a subject airway interface and subtracting the volume of $G_n$.

In one embodiment of the devices described above, the output from a volume controller $VC_n$ is a based on PID control algorithm, for example an error signal for a respective $T_{current}$ is generated based a weighted sum of $e_n$ for the respective $T_{current}$, the derivative of $e_n$ for the respective $T_{current}$ and the integral of $e_n$ for the respective $T_{current}$.

Depending on the application, the cumulative inspired volume of respiratory gas may be constituted by the volume of a part of an inspiratory cycle, a full inspiratory cycle or a series of, parts of or full, inspiratory cycles.

In one embodiment of a device according to the invention the second gas channeling means (e.g. a second gas delivery conduit or added gas delivery conduit) may be fluidly connected to the gas channeling means (optionally a first gas delivery conduit) to deliver $G_n$ into the first gas channeling means e.g. delivery conduit. Alternatively, the first gas channeling means and the second gas channeling means are independently connected to a subject airway interface for coordinately delivering $G_0$ and $G_n$ respectively into the subject airway interface.

It will be appreciated that each of the key method steps for carrying out the invention can be functionally apportioned to different physical components or different computer program products or combinations of both. Furthermore a device according to the invention may comprise one or more physical components in the form of sensors (e.g. flow), gas delivery devices, gas analyzers, gas channeling means, standard electronic components making up a PCB, input devices for setting parameters etc. The various means for carrying out these steps include without limitation one in the same physical means, or different physical means on different devices, the same device or the same device component. Depending on the number of added gases these components may multiplied or where possible shared. A device which is directed to implementing a method of preparing a carbon dioxide ($CO_2$)-containing gas ($G_n$) that is organized for delivery in tandem with a second gas ($G_0$), in manner that composes a respiratory gas ($G_R$) and maintains a target $CO_2$ concentration ($FCO_2^T$) in a cumulative volume of the $G_R$ of interest ($CVG_R^T$), may comprise:

for each successive time point of interest in a growing time period comprising all time points of current interest $T_1$ to $T_{last}$, each successive time point in turn a $T_{last}$:

(a) means for obtaining input comprising or sufficient to compute:
    (i) a cumulative volume of $G_R$ ($CVG_R$) organized for delivery as of $T_{last}$ over all time points of current interest $T_1$ to $T_{last}$; and
    (ii) a cumulative volume of $CO_2$ ($CVCO_2$) organized to compose part of the $CVG_R$ as of $T_{last}$ in all time points of current interest $T_1$ to $T_{last}$; and optionally
  (b) means for using the input obtained to compute a respective incremental volume of $G_n$ that must be delivered as of $T_{last}$ so that the cumulative volume of $CO_2$ in the $CVG_R$ equals $FCO_2^T$; and optionally
  (c) means for controlling a gas delivery means ($GD_n$) so that the respective incremental volume of $G_n$ targets $FCO_2^T$.

In at least one general aspect, the invention is directed to a method for adding at least one added gas ($G_n$) to an inspiratory gas $G_0$, to formulate a respiratory gas ($G_R$) for delivery to a subject, and to maintain a targeted concentration of at least one component of an added gas $G_n$ ($DA_n$) in a volume of the $G_R$ ($DA_R^T$), comprising the steps of:

(a) obtaining input of confirmed incremental volumes of $G_0$ and/or $G_R$ made available for inspiration by a subject with respect to respective time points of interest;
  (b) obtaining input of confirmed incremental volumes of $G_n$ and/or pure $DA_n$ made available for inspiration by a subject with respect to the respective time points of interest;
  (c) at least if required to compute an error signal ($e_n$), obtaining input of the concentration of $DA_n$ in $G_0$ and/or $G_R$ and/or $G_n$ with respect to the respective time points of interest (required where $G_n$ is not pure $DA_n$ or $G_0$ contains $DA_D$); wherein the input obtained is cumulatively sufficient to compute, for successive respective time intervals between contiguous points of interest, an $e_n$ that represents an incremental volume of $G_n$ that must be delivered to the subject with respect to the respective time interval (e.g. for a series of successive time points, each in turn a $T_{current}$, the $e_n$ for the incremental interval ending at a respective last $T_{current}$) so that the cumulative volume of $DA_n$ equals $DA_n^T$;

d) computing $e_n$ for each respective time interval between contiguous time points of interest;

e) providing an output signal to a gas delivery device ($GD_n$) for each respective time interval based on the $e_n$ computed for the respective time interval such that the cumulative volume of $DA_n$ is controlled to target $DA_n^T$.

Each of the individual embodiments of the invention described herein may be adapted to implement the method described immediately above.

In at least one general aspect, the invention is directed to an apparatus for adding at least one added gas ($G_n$) to an inspiratory gas $G_0$, to formulate a respiratory gas ($G_R$) for delivery to a subject, and to maintain a targeted concentration of at least one component of an added gas $G_n$ ($DA_n$) in a volume of the $G_R$ ($DA_n^T$), comprising:

A) means to:
  (a) obtain input of confirmed incremental volumes of $G_0$ or $G_R$ flowed to a subject for time points of interest;
  (b) obtain input of confirmed incremental volumes of $G_n$ or pure $DA_n$ flowed to the subject for the time points of interest;

B) a processor for computing for successive respective time intervals between contiguous time points of interest, an error signal ($e_n$) representing the volume of G, to be made available for inspiration with respect to the respective time interval so that the cumulative volume of $DA_n$ equals $DA_n^T$;

C) means for providing an output signal to a gas delivery device ($GD_n$) for the respective time interval based on the $e_n$ computed for the respective time interval such that the actual cumulative volume of $DA_n$ is controlled to target $DA_n^T$.

Input of the incremental volumes of $G_0$ or $G_R$ and $G_n$ flowed to a subject with respect to respective time points of interest is preferably obtained (e.g. computed) as incremented respective cumulative volumes corresponding to incremented cumulative time intervals comprising the time points of interest, each successive interval cumulating a last new $T_{current}$ or $T_{last}$.

Each of the individual embodiments of the invention described herein may be adapted to assemble or implement the apparatus defined immediately above.

BRIEF DESCRIPTION OF THE FIGURES

FIG. 1c is a schematic representation of one embodiment of a $CO_2$ delivery device in accordance with the invention illustrating, by way of example, optional components and configurations of such a device.

The term "inspiratory gas" denoted $G_0$ refers to any gas to which a gas consisting of or comprising a gas of interest (a component gas) is added. The $G_0$ may be a principal gas provided to a subject for inhalation. For example, a ventilated patient may receive oxygen enriched gas as the $G_0$. The $G_0$ may also be one or more gases consisting or comprising desired component gases which may be individually or collectively considered a $G_0$ with reference to another component gas. Accordingly the invention is concerned with but not limited to conditioning an inspiratory gas in the sense only of a principal gas and in one embodiment of the invention several added gases may be channeled into a manifold and each or the combination of several of them may be an inspiratory gas with reference to a particular component gas. Therefore, the invention contemplates that the necessary volumetric information is ascertained to track actual volumes of the component gas(es) of interest and the volume of gas e.g. the $G_0$ or $G_R$ into which a component gas has been diluted.

The term "volume sensor" (which may also be referred to as a "volume sensing means") means any device that can be used to directly or indirectly determine the volume of a gas that has passed through a breathing circuit or particular conduit thereof, typically with respect to a reference location in a breathing circuit. The invention contemplates that this can be accomplished by a variety of types of hardware including a flow meter, a gas concentration sensor (for example, a certain amount of any first gas of known composition can be inferred to have been delivered past a reference point if mixed with any second gas of known composition and volume by ascertaining the concentration of the first gas in a mixture of the first and second gases), a pressure transducer (for example, an added gas is sourced from a tank of fixed volume, and a pressure transducer in the tank could be used to determine the volume obtained from the tank).

Figure 1A:
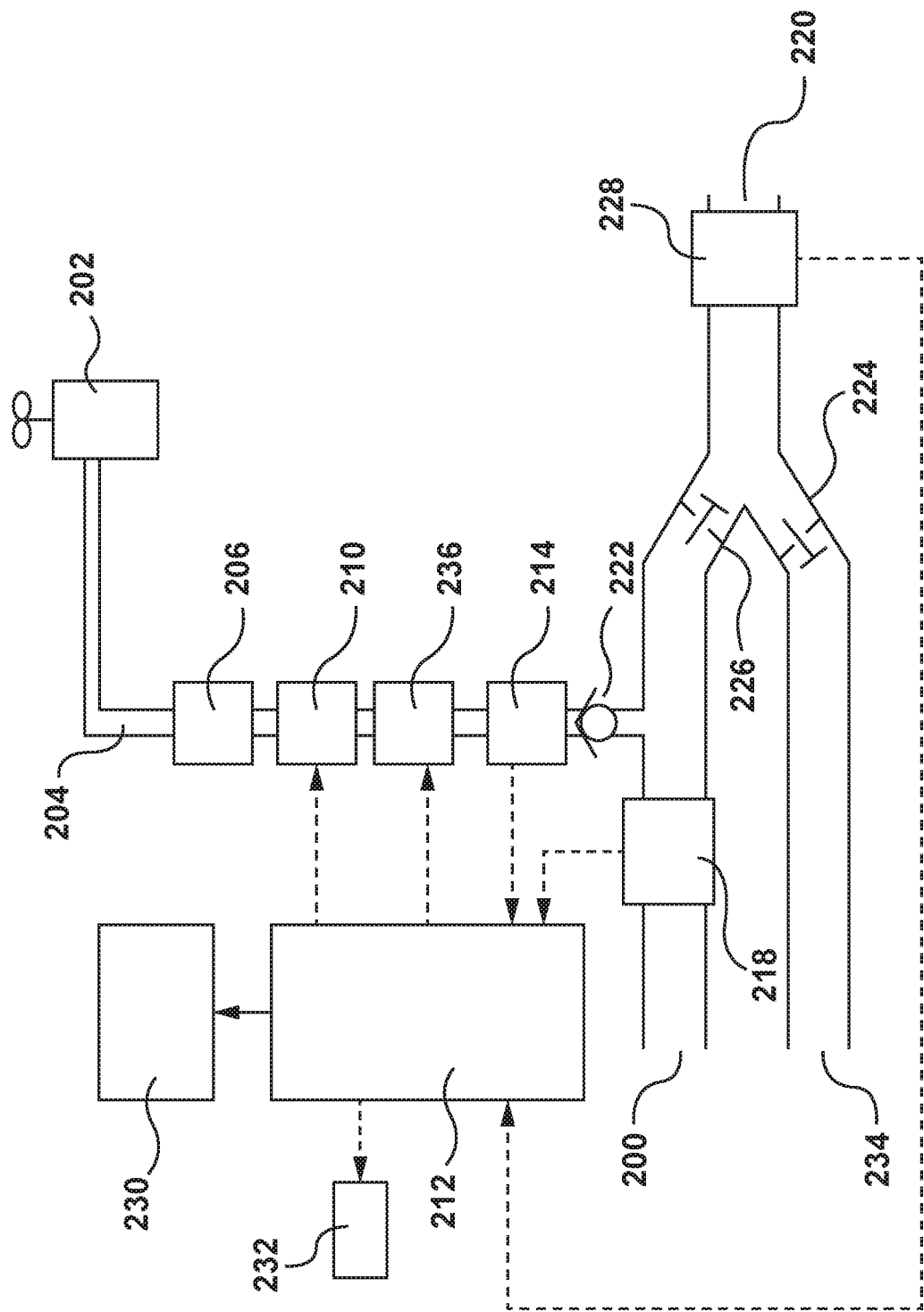
FIG. 1a is a schematic representation of one embodiment of a $CO_2$ delivery device in accordance with the invention illustrating, by way of example, optional components and configurations of such a device.
Figure 1B:
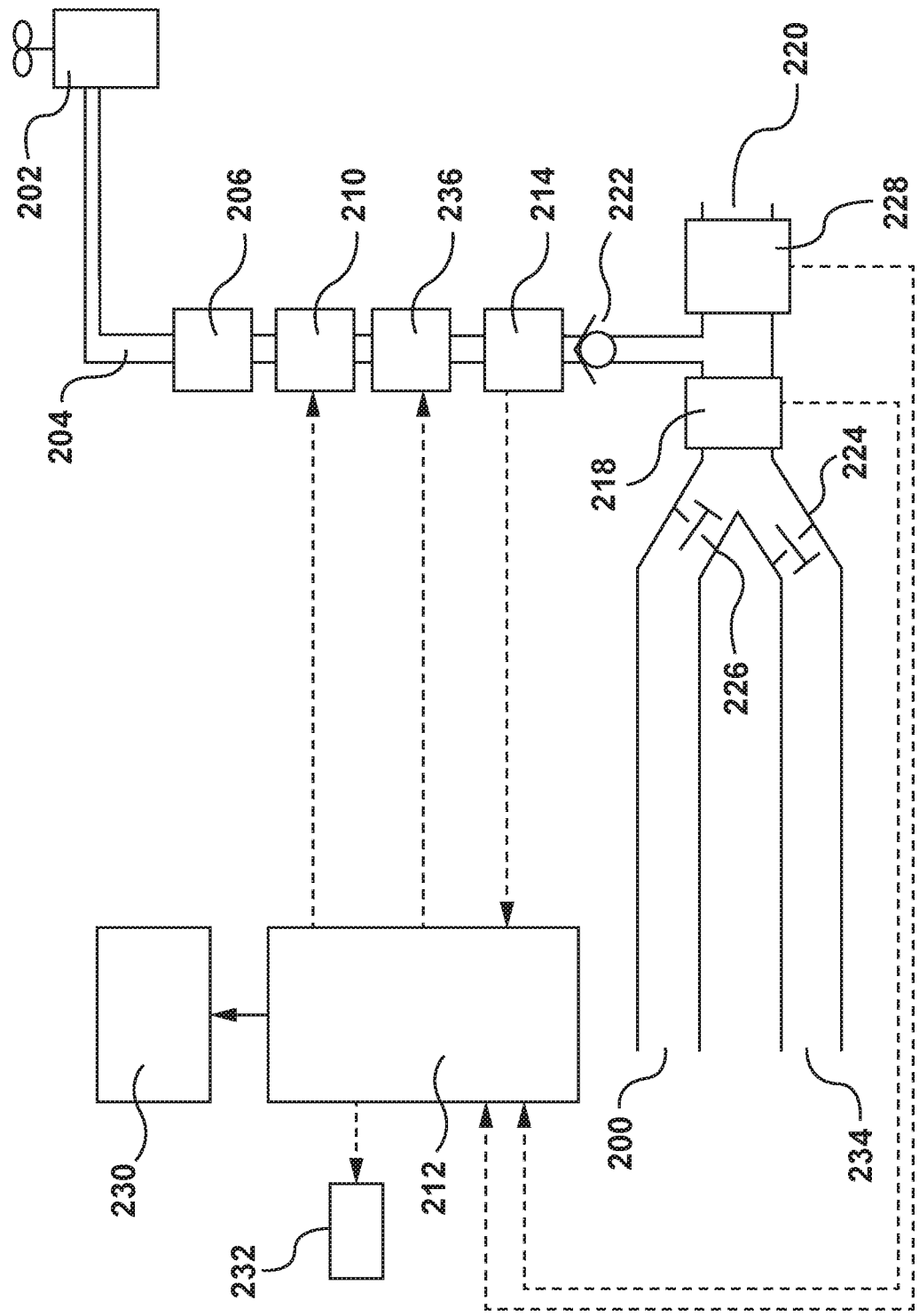
FIG. 1b is a schematic representation of one embodiment of a $CO_2$ delivery device in accordance with the invention illustrating, by way of example, optional components and configurations of such a device.

As shown in FIGS. 1a, 1b and 1c, a system for adding $CO_2$ to an inspiratory gas stream is exemplified by delivering controlled amounts of $CO_2$ into a $G_0$ channeling means exemplified in the form of an inspiratory limb 200 of a breathing circuit. A $CO_2$ supply means, exemplified by tank 202 of pressurized $CO_2$, is illustrated. The $CO_2$ is carried by a conduit 204 made of inert tubing (does not react with $CO_2$ and preferably other optional components of the gas $G_n$ in the tank). Gas leaving the tank of pressurized $CO_2$ is controlled by one or more flow regulators (206) for reducing the pressure of the gas coming out of the tank 202. For example, the pressure may be first be reduced by a single pressure regulator 206, or may be initially reduced to a range acceptable for a miniature pressure regulator, which in turn reduces the pressure of gas Gn further (e.g. $CO_2$) to that required at the inlet of a gas delivery means 210, for example a means for delivering variable incremental volumes of $CO_2$ e.g. a valve that opens proportionally to a control signal (referred to herein as a proportional flow control valve or proportional control valve). Alternatively, a two way solenoid 236 (illustrated in FIG. 1 for a different function) can be turned on an off intermittently to accomplish a form of gas delivery volume control. A pump or blower may serve the purpose in some instances. A computer, optionally in the form of microcontroller 212, optionally incorporates a controller (e.g. a PID controller) for controlling the output signal to the proportional control valve 210. The microcontroller 212 receives input and provides output via signal carrying means shown (with broken lines) as signal lines. Most importantly this input comprises: (1) the output of a sensor means or sensor 214 which serves to determining the actual volume (a "volume sensor") of $CO_2$ output by the proportional flow control valve 210. This volume sensor is optionally a flow meter 214 whose instantaneous or total output is integrated to get the incremental volume of inspired $CO_2$, or the total accumulated volume of inspired $CO_2$, respectively; (2) the output of a second "volume sensor" exemplified as an inspiratory flow meter 218 (output of the respiratory flow meter is integrated to get the accumulated volume of inspired inspiratory gas $G_0$) for determining the actual volume of gas being delivered, for example at a selected junction in the inspiratory limb 200. The inspiratory limb 200 leads to a patient connection 220 which is or leads to a mask, endotracheal tube, etc. (not shown) generically referred to for convenience as a subject airway interface. Measurements made by the inspiratory flow meter made at discrete time points $T_1 \ldots T_{current}$ (each in succession, as time passes, a respective $T_{current}$) enable the controlled delivery of incremental volumes of $CO_2$ which are generally coordinately delivered with the inspiratory gas ($G_0$) stream, in proportioned increments i.e. a calculated amount of $CO_2$ which achieves the targeted fraction of $CO_2$ in the blended volume of respiratory gas $G_R$ ($FCO2^T$) by adjusting the cumulative volume of delivered $CO_2$ to match the integrated flow of the inspiratory flow meter 218 so that the total volume of $CO_2$ gas actually delivered matches $FCO2^T$ with respect to the total volume of the delivered respiratory gas of interest (delivered over an incrementally growing time period $T_{variable}$). Optionally, a check valve 222 (e.g. Beswick CKVU) prevents back flow through the $CO_2$ delivery line. One-way check valves 224, 226 (e.g. Hans Rudolph 5610) may be constituted by low resistance one-way valves that prevent the patient from expiring back in to the inspiratory limb 200, and from inhaling via expiratory limb 234. These one way valves (224, 226) also protect the respiratory flow meter 218 and minimize circuit dead space.

As shown in FIGS. 1a, 1b and 1c, for safety purposes a $CO_2$ analyzer may be used to continuously monitor the inspired and expired fractional concentration of $CO_2$. As described herein, a gas analyzer may also be indirectly used to a volume of gas passing by its location to the extent that a more diluted or concentrated gas may be used to determine what volumes of gas were mixed.

In one embodiment illustrated, for example in FIG. 1a, the microcontroller 212 reads a target % of $CO_2$ ($FCO_2^T$) and all the signals from the sensors and sends suitable control signals to the valve 210 and thereby implements suitable valve control (e.g. PID control). A monitor 230 displays information to the operator and a visible or audible signal generator 232 (e.g. a buzzer) may be used for safety to notify an operator if something goes wrong. In terms of safety features the microcontroller 212 may continuously receive input from the $CO_2$ analyzer 228. If inspired and/or expired $CO_2$ is high for a defined period of time then an optional two-way solenoid valve 236 may be closed, the proportional flow control valve 210 may be closed, and the buzzer 232 excited.

FIGS. 1a, 1b and 1c illustrate different configurations related to the placement of flow sensor 218. In a standard configuration, shown in FIG. 1a, when the inspiratory limb is connected to a ventilator (not shown) flow sensor may not accurately reflect the tidal volume of gas actually entering the patients lungs because the flow sensor 218 measures a compressible volume of gas that is compressed in and expands the tubing more proximal to the subject. Gas flowing through the flow sensor 218 may flow around the Y connection through to the expiratory limb 234. On the other hand, as illustrated in FIG. 1b, the placement of a flow sensor 218 at the mouth (proximal to the patient connection 220) adds dead space which may impair carbon dioxide elimination, especially in children and small adults. Furthermore, it adds bulk and weight to the patient airway interface. As illustrated in FIG. 1c, a cross-bridge 208, connecting the inspiratory 200 and expiratory 234 limbs, causes the flow sensor 218 to see only gas destined for inspiration by the patient as the compressible volume flows through the cross-bridge preventing passage through the flow sensor 218 or in a sense by-passing the flow sensor 218. Optionally, the $G_0$ gas channeling means includes a flow-sensor by-pass means, such as described above, for obtaining an accurate measurement of $G_0$ tidal volume actually flowing to the patient. This form of cross-bridge or by-pass means between inspiratory and expiratory sides can also be present in the ventilator such that a flow meter downstream thereof (towards the patient) in the tubing leading out to the connection to the inspiratory limb of a breathing circuit measures accurate tidal volumes flowing to the patient.

Figure 2:
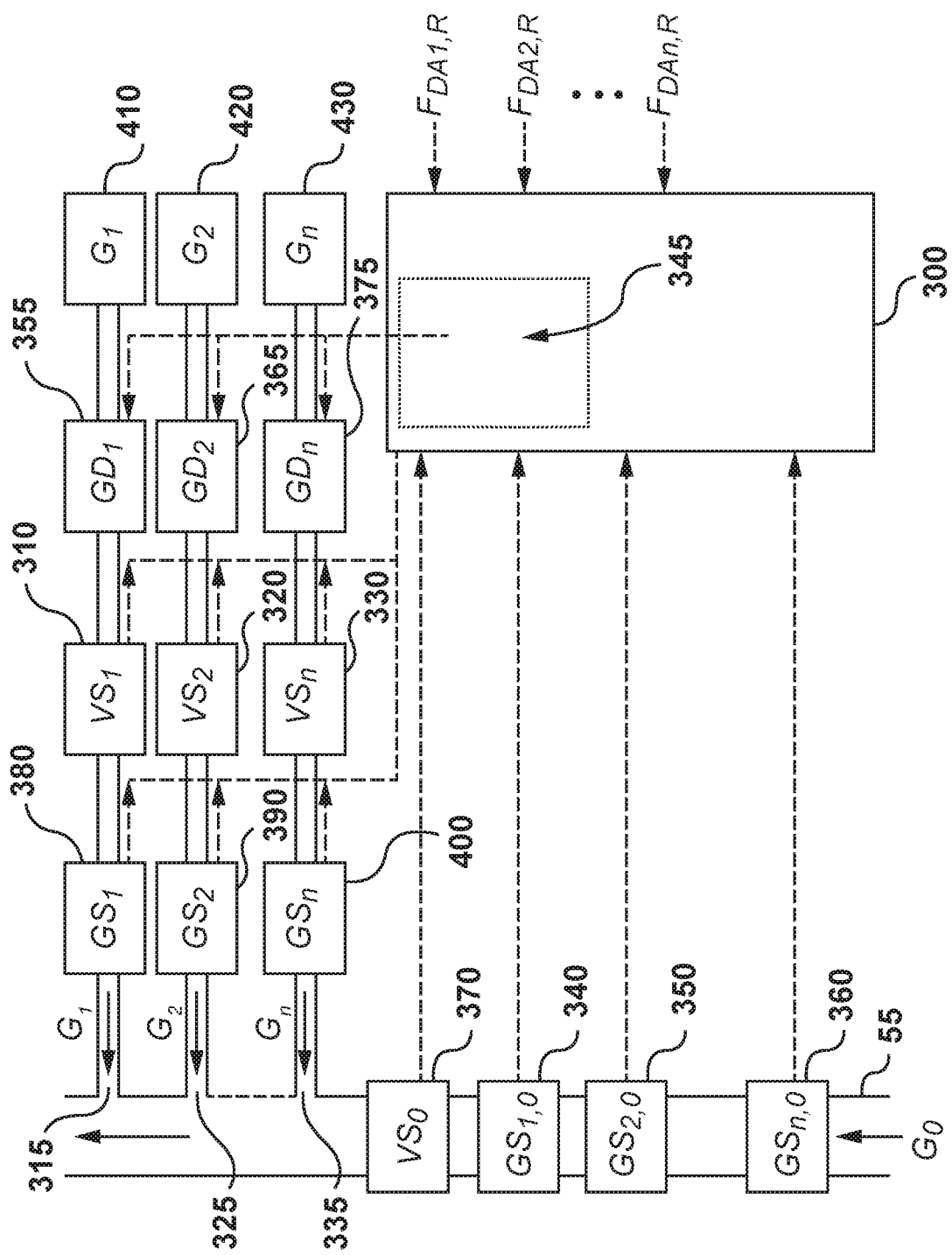
FIG. 2 is a schematic representation of one embodiment of a $CO_2$ delivery device in accordance with the invention illustrating an optional scheme for organizing the flow of several added gases $G_1$ to $G_n$ (directly into the $G_0$ stream) and relevant inputs into and outputs from a computer programmed to implement this embodiment of the invention.

As shown in FIG. 2, according to one embodiment of an apparatus according to the invention several added gases $G_1$ to $G_n$ sourced from gas sources 410, 420 and 430, respectively, may optionally be directly added into the $G_0$ stream. A volume sensor ($VS_0$) 370 is operatively associated with the $G_0$ delivery conduit 55 and is optionally located in the $G_0$ conduit 55, optionally along with respective gas analyzers $GS_{1,0}$ to $GS_{n,0}$ (340, 350, 360) for each of the respective added gases which gases may be present in the inspiratory gas $G_0$. Relevant inputs into and outputs from a computer 300 programmed to implement this embodiment of the invention include: inputs from optional gas analyzers $GS_{1,0}$ to $GS_{n,0}$ (340, 350, 360) and $GS_1$ to $GS_n$ (380, 390, 400) (needed where the fractional concentration of gas of interest in an added gas is unknown or optionally for enhanced safety) and inputs from volume sensors 310, 320, 330, (as broadly defined herein) optionally located in the respective added gas delivery conduits 315, 325 and 335. Inputs of fractional concentrations of the respective component gases $F_{DA1,R}$-$F_{DAn,R}$ enable a controller 345, optionally integrated as part of the computer 300, to direct outputs to respective gas delivery means $GD_1$ to $GD_n$ (355, 365, 375) based on the actual incremental volumes of gas delivered by the gas delivery means as determined via the respective volume sensors $VS_0$ (370) and $VS_1$ to $VS_n$ (310, 320, 330). It will be appreciated that a component gas of interest does not need to be $CO_2$ and may be any gas such $O_2$, Xe, He, $H_2$, NO, $N_2O$, $H_2S$, CO, SF6, an anesthetic, etc. In, for example, a compressed gas form, one or more such gases can be added to the $G_0$ gas to compose a respiratory gas $G_R$. The term $DA_n$ is generically used herein to refer to a component gas of interest and any reference herein to carbon dioxide, except where the context necessarily implies that carbon dioxide is being referred to specifically, may be replaced by a reference to $DA_n$ or any other specific component gas.

A device according to the invention may therefore comprise a wider or narrower variety of components that may be particularly useful or more readily substitutable for implementing a particular application of the invention. Furthermore, depending on a suitable range of deliverable volumes of gas in question, optionally attuned to a particular size range of a breath (e.g. for a premature human infant or small animal) the sizes and ranges of accuracy of components may be differently selected according to well understood design criteria.

In terms of optional embodiments, the $GD_n$ is optionally a proportional solenoid valve metering the release of $G_n$ from a pressurized gas source. The invention also encompasses intermittently turning on and off a two-way solenoid valve metering the release of $G_n$ from a pressurized gas source. Optionally, the $GD_n$ can be a gas pump, blower, or injector connected to a pressurized or unpressurized reservoir of $G_n$.

Input of $CVG_n$ actually delivered during $T_1 \ldots T_{now}$ is obtained via a volume sensor ($VS_n$) operatively associated with a $G_n$ delivery conduit. Input of $CVG_0$ actually delivered during $T_1 \ldots T_{now}$ may be obtained via a second volume sensor ($VS_0$) operatively associated with a $G_0$ delivery conduit. A volume sensor can be constituted by any hardware for directly or indirectly measuring a volume of gas, for example, a spirometer, or a flow transducer or gas analyzer from which the flows of gases can be deduced (and then computing the integral of the flow).

The inputs, computations, and outputs described in the aforementioned method can be carried out by a variety of signal processing means including, but not limited to, a programmable processor, programmable microcontroller, dedicated integrated circuit, programmable integrated circuit, discrete analog or digital circuitry, mechanical components, optical components, or electrical components.

The $VC_n$ can be implemented by a variety of signal processing means including, but not limited to, a programmable processor, programmable microcontroller, dedicated integrated circuit, programmable integrated circuit, discrete analog or digital circuitry, mechanical components, optical components, or electrical components.

A $G_n$ gas channeling means, optionally in the form of a $G_n$ delivery conduit, is optionally adapted to be operatively associated with or directly fluidically connected to a $G_0$ channeling means, for example, a $G_0$ delivery conduit such as the inspiratory limb of a breathing circuit, a patient airway interface, a manifold for receiving multiple gas connections, or a connector interconnecting one or more of the above.

In one embodiment of the invention, all inputs, computations, and outputs are performed on a general purpose microcontroller. The $G_n$ is a pressurized gas containing a known, fixed concentration of $DA_n$. A rapid $DA_n$ analyzer is operatively associated with the $G_0$ delivery conduit to ascertain the concentration of $DA_n$ in $G_0$. A $VS_n$ is implemented by integrating the output of a flow transducer operatively associated with the $G_n$ delivery conduit. A $VS_0$ is implemented by integrating the output of a flow transducer operatively associated with the $G_0$ delivery conduit. The $VC_n$ may be a PID controller implemented on a general purpose microcontroller. For each $T_{current}$, $GD_n$ receives a weighted sum of the output of $VC_n$ and $G_n^P$. The incremental $G_0^P$ predicted to be delivered in the time interval $\Delta T$ between the respective $T_{current}$ and a ensuing time point $T_{current+}$ is equated with the incremental volume of $G_0$ delivered in the time interval $\Delta T$ ending at $T_{current}$. The $GD_n$ is implemented with a series of pressure regulators and a proportional solenoid valve metering the release of $G_n$ from the pressurized source. The $G_n$ delivery conduit is directly fluidically connected to the $G_0$ channeling means so that the $G_n$ is directly delivered into the $G_0$ stream.

Figure 3:
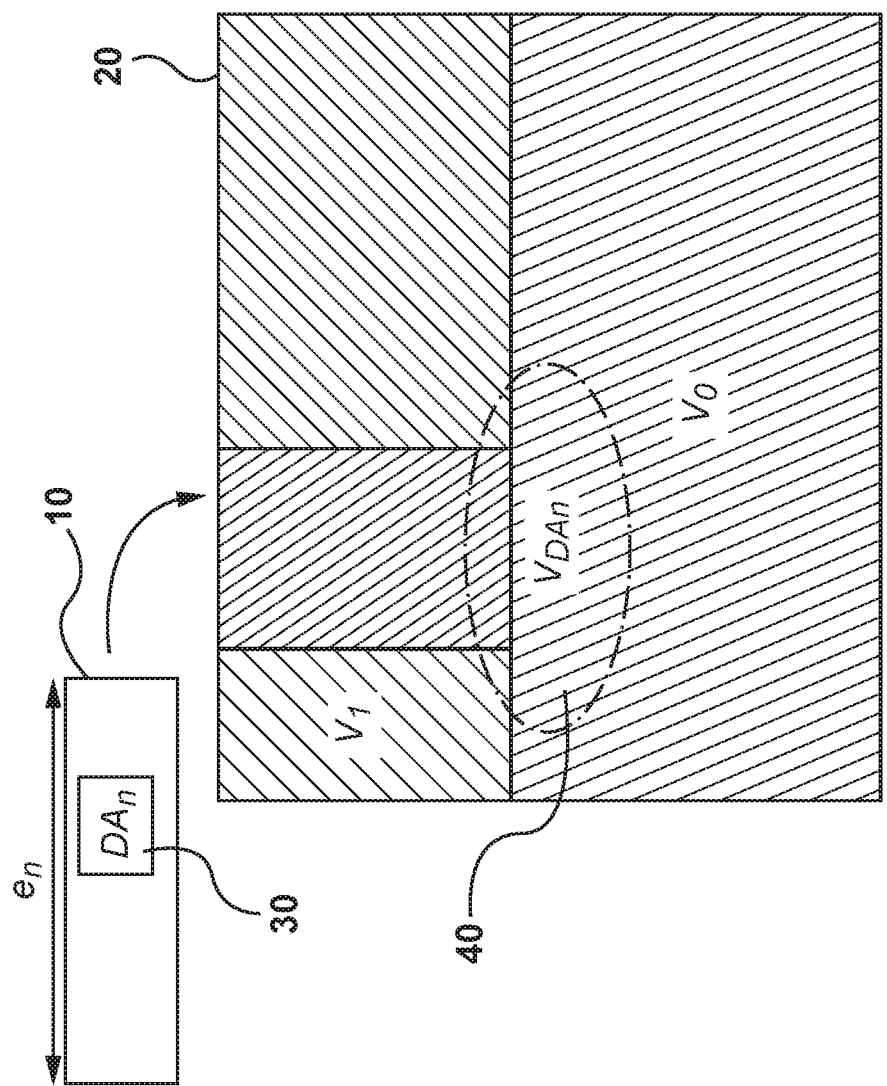
FIG. 3 is a schematic representation useful for describing key volumetric control considerations underlying the presently disclosed scheme for adding one or more gases ($G_n$) containing a desired component gas $DA_n$ (e.g. $CO_2$) to an inspiratory gas ($G_0$) stream according to one embodiment of the invention.

As shown in FIG. 3, implementation of the invention, preferably takes into account a cumulative volume of all of the several components of a respiratory gas $G_R$ 20 delivered to a subject including the respective volumes of one or more added gases $V_1, V_2 \ldots V_n$ which are coordinately delivered with an inspiratory gas ($G_0$) stream, in proportioned increments i.e. a calculated amount of $G_n$ 10 which achieves the targeted fraction of $DA_n$ 30 in a volume of $G_R$ ($DA_n^T$) is consistently added to keep step with one or more recent incremental amounts of $G_0$ and other added gases flowed to the subject. The term "coordinately" means involving coordination so as to update the fraction of $DA_n$ in a volume $G_R$ to a desirable extent in terms of frequency and accuracy. Optionally, keeping step with new incremental volumetric amounts of delivered $G_0$ takes full advantage of the capabilities of the hardware of choice. For example, typical cost-effective hardware may be capable of delivering a proportioned amount of $G_n$ (relative to an updated cumulative volume of $G_0$ including the last confirmed incremental volume of $G_0$ flowed to the subject) containing a known/determined fraction $DA_n$ to match $DA_n^T$—every millisecond. The curved arrow is used to imply controlled and confirmed (via some form of sensor) volumetric addition (e.g. via an appropriately controlled gas metering device e.g. a proportional solenoid under PID control) of a discrete corrective volume of a gas $G_n$ 10 containing a component gas of interest ($DA_n$) to a confirmed total volume of delivered gas (including $V_1 \ldots V_n$, $V_0$ and optionally $DA_n$)–the confirmed cumulative $G_R$ volume (confirmed via cooperative action of a plurality of sensors of a broadly varying type and location of placement). It is understood that $G_n$ may be made up entirely (100%) of $DA_n$. As described herein, incremental amounts of $DA_n$ flowed to the subject are preferably at least "retrospectively corrective" to target $DA_n^T$, and as described below may optionally be a "predictively corrective" component (inasmuch as a predictive strategy can be termed "corrective" when serving the optional purpose of facilitating a retrospectively corrective strategy).

$V_{DAn}$ (represented by the oval area 40) is an accumulated volume of the component gas of interest that forms part of the volume of $G_R$ 20 delivered in virtue of being added at full concentration ($G_n$ is 100% $DA_n$) or blended (as illustrated) into one or more of $V_1, V_2 \ldots V_n$. $DA_n$ may optionally also be a component of inspiratory gas $G_0$. An error signal $e_n$ according to a simple embodiment of the invention is the volume 10 of gas $G_n$ that is needed to be delivered (based on what on has been "definitively" already delivered) to carry with it enough of the component gas of interest to ensure that the resulting amount of this component gas in a volume of the respiratory gas $G_R$ is incrementally maintained (subject to hardware time lags) and therefore consistently (to the extent practicable or desired) in the same proportion vis-à-vis the total volume of "definitively" delivered $G_R$ regardless of the changing total volume of gas that has been delivered to the subject. "Definitively" delivered amounts of $G_n$ and $G_R$ are not amounts that the hardware would have delivered if responding perfectly to flow settings but volumes that requisite "sensors" determine have indeed flowed through the pertinent gas delivery conduits. The term "definitively" is used superfluously in the present description of FIG. 3 for extra emphasis to distinguish amounts theoretically flowed to the subject (the term "delivered" when used to refer to a volume of a gas implies a volume measured by some form of device—generically called a "volume sensor"—that directly or indirectly measures or enables volume computation—"delivered" is considered to sufficiently distinguish a "flow setting" or other "unverified delivery" modality used in prior devices). Variations on the above-described basic approach of "incrementally" correcting to a desired relative proportion—delivered $DA_n$ in delivered $G_R$ (retrospective) include adjunct "predictive correction" strategies for optimizing the error signal. Sub-optimal correction on the other hand may vary the size range of volumetric increments of $G_0$ being corrected—the invention is best exploited by correcting small increments of newly delivered gas, optionally, but not necessarily, the smallest increments possible having regard to inherent limitations the hardware available or selected (e.g. cost effective) for use. In one embodiment, adjunct predictive correction involves predicting how much the volume of $G_R$ will grow from delivery of $G_0$ in one or more ensuing increments of time (typically by predicting one or more ensuing incremental volumes of $G_0$ based one or more recent $G_0$ sensor readings) and computing an accommodative error signal even before the new gas is definitively delivered into the cumulative volume of $G_R$. According to another embodiment, the computed $e_n$ may take into account, only amounts of $G_0$ and $G_n$ definitively delivered. Variations on "computing" the error signal, involving a predictive correction factor are understood as adjunct strategies that are not inconsistent with baseline retrospective volumetric correction that broadly defines the invention in one aspect. Aside from "computing" a baseline error signal retrospectively, a controller, for example a PI or PID controller, would conventionally be used to appropriately implement the corrective $e_n$. Accordingly, compensating for hardware limitations inherent in delivering $e_n$ may be seen to represent a distinct aspect of the totality of the volumetric corrective measure that would be expected to be implemented by an engineer in implementing the invention.

It may be appreciated that the strategy of the invention may be implemented to a useful extent if the incremental gas proportioning is consistent in the first part of inspiratory cycle (see FIG. 5) even if done in less than optimally small sequential as opposed to sporadic and/or wider spaced time increments. The first part of the inspiratory cycle of interest is the volume that destined to enter the alveoli as opposed to dead space volumes. Furthermore, in theory, the desired or chosen fraction of $DA_n$ in $G_R$ may be so small that computational inclusion of $DA_n$ as a necessary part of $G_R$ could be obviated for small cumulative volumes of $DA_n$. Accordingly, the formulas and strategic approaches presented herein address embodiments of and options with respect to best and/or most universal practices and don't purport to cover all sub-optimal or circumventive strategies of exploiting the invention.

Figure 4:
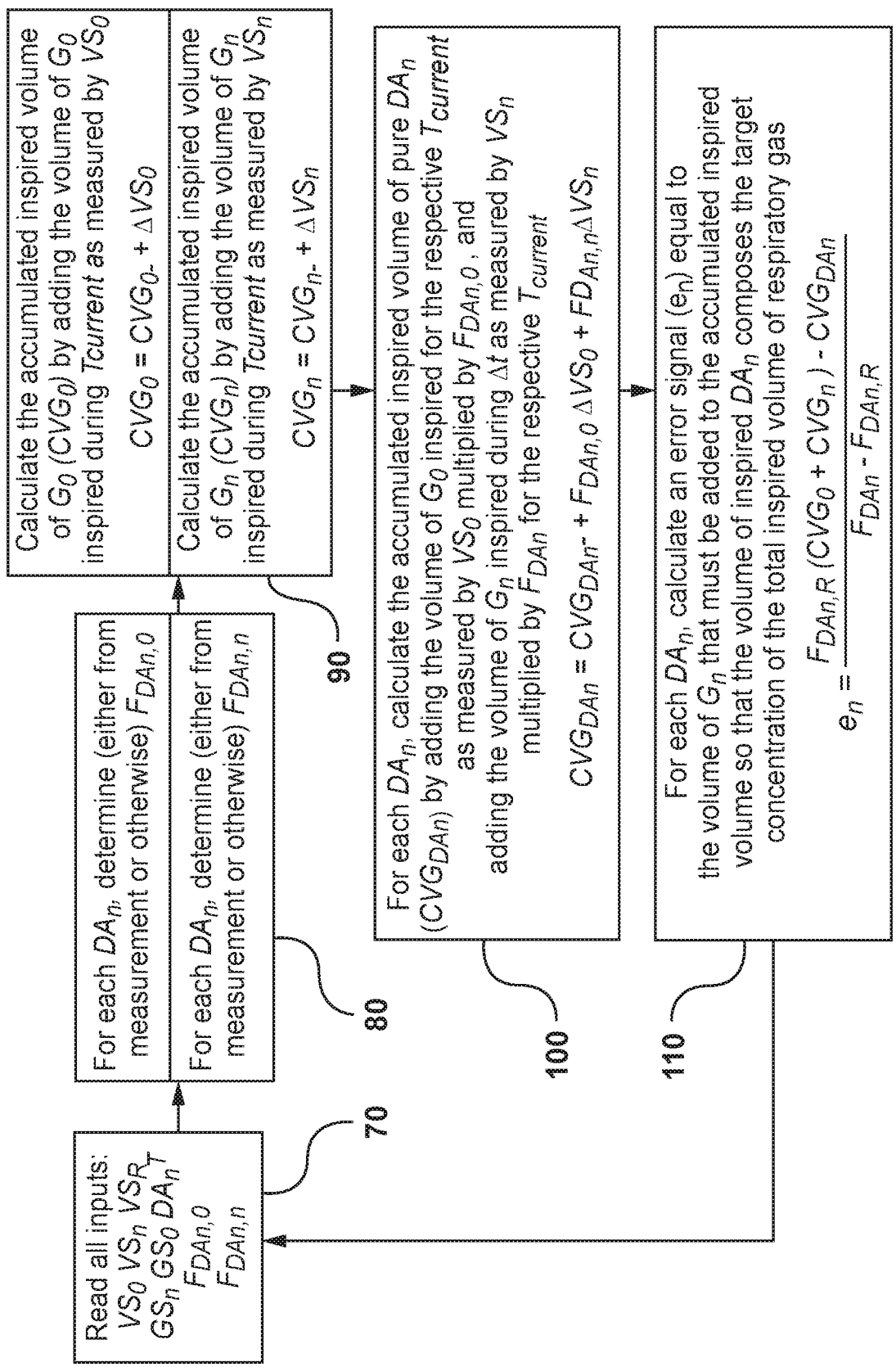
FIG. 4 is a flow chart illustrating one embodiment of implementing a method according to the invention and related computer processing steps.

As shown in FIG. 4, one embodiment of a method (and related algorithm) according to the invention, may be expressed as a series of steps carried out with respect to each time increment $T_{current}$ (optionally a time increment that is optimized having regard to time delays of the computer, controllers, gas delivery means and sensors (volume, gas analyzer), wherein the computer:

1. Reads inputs as exemplified in FIG. 4 (70)
2. Calculates (90) the accumulated inspired volume of $G_0$ ($CVG_0$) by adding the volume of $G_0$ inspired at the respective $T_{current}$ (to the accumulated volume of $G_0$ determined as at the previous respective $T_{current}$ ($CVG_{0-}$)) as measured by $VS_0$
3. Calculates (90) the accumulated inspired volume of each $G_n$ ($CVG_n$) by adding the volume of $G_n$ inspired for the respective $T_{current}$ (to the accumulated volume of $G_n$ determined as at the previous respective $T_{current}$ ($CVG_{n-}$)) as measured by $VS_n$
4. For each $DA_n$, determines (either from measurement or otherwise) $F_{DAn,0}$ (80)
5. For each $DA_n$, determines (either from measurement or otherwise) $F_{DAn,n}$ (80)
6. For each $DA_n$, calculates (100) the accumulated inspired volume of pure $DA_n$ ($CVG_{DAn}$) by adding the volume of $G_0$ inspired the respective $T_{current}$ as measured by $VS_0$ multiplied by $F_{DAn,0}$ at $T_{current}$, and adding the volume of $G_n$ inspired during the time interval ending in $T_{current}$ as measured by $VS_n$ multiplied by $F_{DAn}$ during the respective $T_{current}$ (it will be appreciated that this type of computation may accomplished by calculating (90) the accumulated inspired volume of each $G_n$ ($CVG_n$) by adding the volume of $G_n$ inspired during the respective $T_{current}$ especially where fractional concentration of $DA_n$ in $G_n$ is constant or is consistently 100%).
7. For each $DA_n$, calculates (110) an error signal ($e_n$) equal to the volume of $G_n$ that must be added to the accumulated inspired volume of respiratory gas ($CVG_R$) so that the volume of inspired $DA_n$ composes the target concentration of $DA_n$ ($DA_n^T$ or $F_{DAn,R}$) in $CVG_R$ (optionally the projected total inspired volume of respiratory gas at $T_{current+}$)

$$\frac{CVG_{DAn} + F_{DAn} \cdot e_n}{CVG_0 + CVG_n + e_n} = F_{DAn,R}$$

$$e_n = \frac{F_{DAn,R}(CVG_0 + CVG_n) - CVG_{DAn}}{F_{DAn} - F_{DAn,R}}$$

8. Delivers a signal to each $GD_n$ generated from the weighted sum of the current value of $e_n$, the derivative of $e_n$, and the integral of $e_n$ (not shown).

The term $DA_n$ (and, as applicable, terms which reference $DA_n$ such as $F_{DAn}$ and $CVG_{DAn}$) may for convenience be understood to be used expansively to reference embodiments of the invention in which there is one $DA_n$ as well as multiple $DA_n$s (more precisely $DA_{1-n}$) since $DA_n$ in the latter scenario can be understood, if interpreted in a restrictive sense, to mean the last in the series 1 to n. In context, where more than one "$DA_n$" is delivered as part of the cumulative volume of respiratory gas $G_R$, with respect to each "$DA_n$" (strictly speaking each respective $DA_1$ . . . $DA_D$), each other "$DA_n$" can be understood to be taken into account as part of the $G_0$ and hence the aforementioned generic formula for the error term $e_n$ should be understood broadly to be generically applicable to each respective "$DA_n$" ($DA_{1 ... n}$) based on the assumption that the volumes of the added gases other than the one for which the computation is being made are taken into account as part of the $G_0$. The (+) sign with reference to a time point is used herein to refer to a future time point (not yet a $T_{current}$) for which actual delivered (output by a $G_n$ specific gas delivery device or ventilator) volumes of a component gas and $G_0/G_R$ have not been ascertained. A minus (−) sign may be used to refer to a time point before a respective $T_{current}$ e.g. the most recent $T_{current}$ for which actual delivered (output) volumes have been ascertained.

It will be appreciated from the foregoing description that $e_n$ may be a corrective volume to bring the concentration of $DA_n$ in line with $DA_n^T$ as at $T_{current}$ without taking into account the incremental volume of $G_0$ expected to be delivered by the next respective $T_{current+1}$. Alternatively, the computation may take into account the expected incremental volume of $G_0$ expected to be delivered by the next respective $T_{current+}$ and hence the projected total of volume of respiratory gas expected to be delivered by the next $T_{current}$ including the $e_n$ and its $DA_n$ content.

Figure 5:
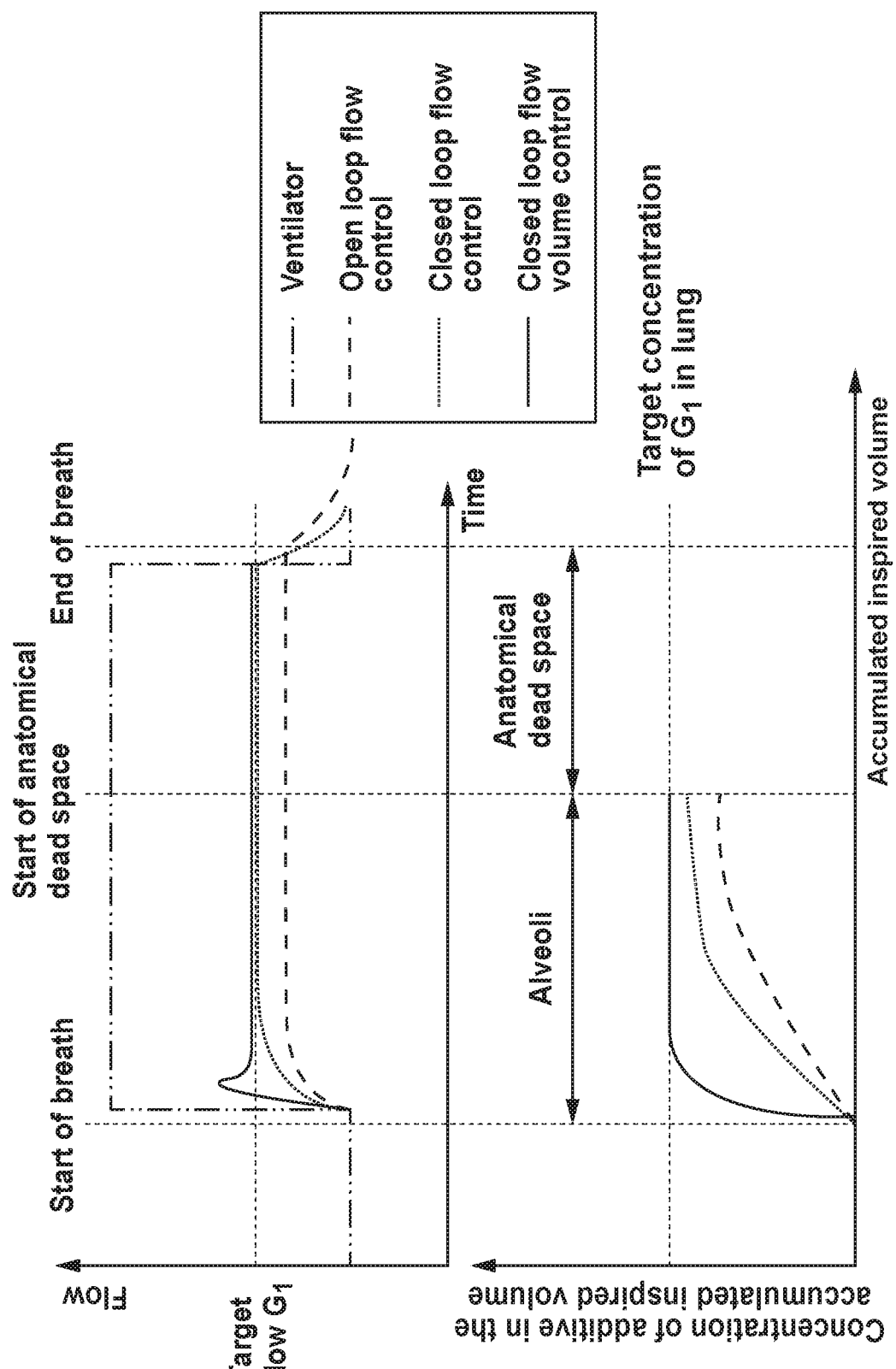
FIG. 5 is an illustration in a graph form of advantages of an embodiment of the invention for adding $CO_2$ to an inspiratory gas stream.

As shown in FIG. 5, panel A, a device according to the invention implements a form of closed loop volume control that enables the flow of $G_1$ to maintain a target concentration of G1 in the total inspired volume, as early as possible in the breath. As shown in Panel B, this is especially important and advantageous with respect to the first part of a breath that fills the alveoli. As seen in Panel B, belated matching of the theoretical flow without later compensation accumulates volumetric error that will not achieve the targeted concentration of $DA_n$ in $G_R$ in the volume of $G_R$ destined to be part of volume of gas entering the alveoli. FIG. 5 is described in more detail below.

In one aspect, the volume of gas containing $DA_n$ is ideally delivered as part of the expanding volume of gas that is alveolar gas and not dead space gas. This is explained with reference to FIG. 5 described in more detail below.

The invention can therefore be understood to be broadly directed to a method for adding at least one added gas ($G_n$) to an inspiratory gas $G_0$, to formulate a respiratory gas ($G_R$) for delivery to a subject, and to maintain a targeted concentration of at least one component of an added gas $G_n$ ($DA_n$) in a volume of the $G_R$ comprising the steps of:
for each of a series of time points of interest (generally time points in which $G_n$ is being coordinately delivered with $G_0$):
  (a) obtaining input of confirmed incremental volumes of $G_0$ or $G_R$ flowed to a subject;
  (b) obtaining input of confirmed incremental volumes of $G_n$ or pure $DA_n$ flowed to a subject;
  c) computing for any respective $T_{current}$ an error signal ($e_n$) equal to the volume of $G_n$ that must be coordinately delivered to the subject with the $G_0$ so that the cumulative volume of $DA_n$ equals $DA_n^T$;
  d) for any respective $T_{current}$ providing an output to $GD_n$ based on the $e_n$ computed for the respective $T_{current}$ whereby the actual cumulative volume of $DA_n$ (generally coordinately delivered with $CVG_0$ as part of $CVG_R$) is controlled to target $DA_n^T$.

Thus in a broader aspect, the present invention relates to a device, method and system for delivering at least one added gas into an inspiratory gas stream to formulate a blended respiratory gas in a manner that continuously maintains a target concentration of the added gas in a volume of inspired respiratory gas, for example, over the course of a breath or a volumetrically definable part thereof or a series of partial or full breaths. The inspiratory gas may be a principal gas stream delivered to a patient such as air optionally having an enhanced oxygen content or air and oxygen combined with an anesthetic gas delivered by a ventilator or anesthetic machine but may also be comprised of several additive gases delivered individually or in blended form according to a method/device according to the invention.

A goal of most respiratory gas blenders is to deliver a target concentration of an additive gas into the inspired stream. Previously, this has been done by measuring the inspiratory flow and sending a signal to a flow controller to provide a flow of additive gas proportional to the inspired stream. Such a "flow-based control" system essentially tries to maintain the instantaneous concentration of the additive gas in the inspired gas at the target value. However, due to practical limitations of flow transducers and flow controllers, most notably finite response times, it is not possible for a flow controller to exactly "track" the inspired gas stream. Therefore, at any time during the breath, the instantaneous concentration of additive gas in the inspired stream may not be equal to the target concentration. Moreover, the overall concentration of additive gas in the accumulated inspired volume will not be equal to the target concentration. Furthermore, the design of previous respiratory gas blending systems overlooks that it is the concentration of additive gas, by volume, in the volume of inspired gas that reaches the alveoli that is the most important factor in many physiologic, therapeutic and/or diagnostic contexts.

The simplest gas blending systems try to match the flow of additive gas to the inspired stream with an open loop signal to a flow controller. That is, the actual flow of additive gas delivered by the flow controller is not monitored. If there is a systematic error/offset in the flow delivered by the flow controller, the flow of additive never reaches the target flow rate. Therefore, the instantaneous concentration of additive in the inspired stream never reaches target, and the concentration by volume in the accumulated inspired gas is always in error.

More complex blending systems try to match the flow of additive gas into the inspiratory gas stream with a closed loop signal to a flow controller. That is, the actual flow of additive gas delivered by the flow controller is monitored. If there is a systematic error/offset in the flow delivered by the flow controller, the signal to the flow controller is adjusted until the flow of additive reaches the desired flow rate. Therefore, the concentration of additive in the inspired stream may reach the target value as the breath proceeds, but because of an obligatory delay in response of the flow controller for the additive gas, the overall concentration by volume will always be less than the target concentration set at the beginning of the breath.

In one aspect, the present invention contemplates a control system in which the overall concentration of additive gas, in the volume inspired gas entering into the alveoli, reaches the desired value.

The invention contemplates that one or more additional gas delivery conduits may be operatively connected to or otherwise operatively associated with (via coordinated delivery into an airway interface) the $G_0$ delivery conduit for coordinately delivering a controlled volume of an added gas $G_n$ (or controlled volumes of a plurality of added gases $G_1$ to $G_n$) with the $G_0$ stream, wherein each $G_{1-n}$ is at least partially composed of a respective desired additive gas ($DA_{1-n}$). In one embodiment, each gas delivery conduit carrying an added gas is operatively associated with a volume controller for controlling the volume of gas coordinately delivered with the $G_0$, a volume sensor operatively associated with the added gas delivery conduit for continuously measuring the accumulated volume of the added gas. Optionally, where the fractional concentration of the added gas in $G_0$ is not known, a means (for example a gas analyzer), operatively associated with the $G_0$ delivery conduit, may be employed to measure, optionally continuously, the fraction of the added gas in the $G_0$ delivery conduit. Optionally, for example for a given $G_n$, where the fractional concentration of the desired added gas in $G_n$ ($F_{DAn}$) is not known, a means, operatively associated with the $G_n$ delivery conduit, for example a gas analyzer may be employed to measure, optionally continuously, $F_{DAn}$ in the $G_n$ delivery conduit ($GS_n$). For example, in one embodiment, for a gas $G_n$, the device may comprise:

(1) A volume controller ($VC_n$) for controlling the volume of $G_n$ added to $G_0$ (2) A volume sensor ($VS_n$) operatively associated with the $G_n$ delivery conduit for continuously measuring the accumulated volume of inspired $G_n$ Optionally, where the fractional concentration of $DA_n$ in $G_0$ ($F_{DAn,0}$) is not known, a means, operatively associated with the $G_0$ delivery conduit, to measure continuously $F_{DAn,0}$ in the $G_0$ delivery conduit ($GS_{n,0}$)

(3) A computer that takes input of:
   A target concentration of each $DA_n$ in the accumulated inspired volume ($F_{DAn,i}$)
   The output of $VS_0$
   The output of each $VS_n$
   Each $F_{DAn,0}$ (either known or measured)
   Each $F_{DAn,n}$ (either known or measured)
   And provides output to each $VC_n$.

On inspiration, gas entering the mouth or nose is conducted to the lung through a series of conduits consisting nasopharynx, oropharynx, trachea and bronchi. From the point of view of gas exchange, these are considered conducting vessels directing gas to the alveoli. As these conducting vessels do not contribute substantially to gas exchange, they are termed anatomical deadspace. In an average adult, they consist of about 2 ml per kg of body mass, or about 150 ml for the average adult. The alveoli are small saccules where the gas comes into close contact with blood and gas exchange takes place.

The distribution of gas during inspiration is well understood. At end expiration, the lung volume is smallest. In the course of inhalation gas is drawn through the anatomical deadspace into the alveoli. At end inspiration, the inspired gas is distributed between the alveoli and the anatomical deadspace. Note the last inhaled gas is retained in the anatomical deadspace. Physiologically the alveoli acts like a mixing chamber where the accumulated gases are mixed. The physiologic effect of an inhaled gas is determined by its net concentration once it has mixed in the alveolar space, that is, its fractional volume in the alveoli. Its instantaneous inhaled concentration is only important to the extent that it affects the net volume of that gas in the inspired volume. Although the flow-based controllers can reach an instantaneous target concentration of additive in the inspired stream, they are not directed towards providing a net concentration of a gas in the alveolar space where gas exchange takes place and where the net concentration of the added gas exerts its pharmacologic effect. This is illustrated in FIG. 5. The model is that of a subject being ventilated by a ventilator that provides a square wave inspiratory flow of $G_0$ (this simplest of cases is used for illustrative purposes; the principle herein described applies to any inspiratory flow pattern by a ventilator or via spontaneous ventilation) and a target concentration of component gas 1 ($G_1$). A required flow of $G_1$ is required to attain this target concentration of $G_1$ in the total inspired gas. At the beginning of inspiration the response delay in the flow controller results in a ramp up to target flow. The effect on the $G_1$ concentration of the gas in the alveoli—the cumulative volumetric error resulting from the shortfall in the instantaneous concentration of additive $G_1$ in the inspired stream during inhalation—is illustrated in the lower part of the figure. Note that the difference in the volume of $G_1$ delivered to the alveoli, as represented by the difference between the between the curves "target flow $G_1$" and that of the flow-based controllers, results in the volumetric concentration of $G_1$ in the inspired gas reaching the alveoli always being less than the desired concentration. The instantaneous concentration of additive in the inspired stream is in greatest error at the start of the breath. Therefore, early terminations of the breath increase the discrepancy between desired concentration and actual concentration of $G_1$ in the volume of inspired gas reaching the alveoli.

Previous devices have been designed on the premise that a response delay of a flow-based controller at the start of the breath is mirrored by an overshoot in $G_1$ flow at the termination of the breath. Over the whole breath, this may result in an average alveolar $G_1$ concentration at the desired level if the acceleration and deceleration profile of the breath are symmetrical. However with respect to ventilation, as illustrated in the lower part of FIG. 5, only the initial part of the breath reaches the alveoli. The overshoot in $G_1$ flow at the termination of the breath in our model of a square wave inspiratory flow occurs during exhalation and provides no compensation to the lung concentration. With more sinusoidal inspiratory gas flow, there may be excess flow of $G_1$ as the inspiratory flow of $G_0$ slows down. However, at least part of the terminal aspect of the breath where the compensation takes place with flow-based control always resides in the anatomical deadspace and the increased compensatory flow of $G_1$ does not reach the alveoli.

By contrast, a closed loop volume-based control provides early reconciliation of the $G_1$ volume and the inspired volume of $G_0$ such that the net inspired concentration of $G_1$ is at the desired level very early in the breath. In practical terms, a volume controller according to the invention can provide fully compensated alveolar concentrations of $G_1$ within as little as 10 ml of inspired volume and typically within 20-50 ml. Premature terminations of breaths after this level is reached would not affect the physiologically important net inspired concentration of $G_1$ in the alveolar compartment of the lung.

Furthermore, with respect to the finite response time of any flow controller, the shorter the breath, and the greater the inspiratory flow, the more significant the delay period of the flow controller becomes with respect to providing the overall volumetric concentration of additive gas. Therefore for rapid breathing, where inspiratory flows are high and inspiratory times short, errors of $DA_n$ volumetric concentrations in the alveoli are magnified by response delays of flow controllers. Furthermore, even flow controllers with very rapid response times may still accumulate physiologically important errors of concentrations of $DA_n$, particularly where $DA_n$ is a potent physiologic molecule (defined as having a large physiologic effect for a small change in concentration), in the overall volumetric concentration of $DA_n$ in the accumulated inspired volume.

The system according to the invention operates a closed control loop in order to maintain the concentration of additive, by volume, in the accumulated inspired volume at a target value throughout the breath. At each point in time, the total inspired volume and the total volume of inspired additive is assessed. An error signal is generated equal to the volume of additive that must be added to the inspiratory gas stream so that the overall concentration of additive, by volume, in the gas accumulated in the lung during inspiration will be equal to the target value throughout the breath. The error signal is provided to a volume controller which provides a signal to a gas delivery means (alternatively called a gas delivery device). This maintains the concentration of additive, by volume, in the accumulated inspired volume at the target value throughout the breath.

As described below, the invention contemplates that multiple gases can be combined according to a method of the invention or using a device, computer program product (including any known format in which the requisite program code can be recorded or hard-wired), processor or system according to the invention based on adaptations described herein and evident to those skilled in the art. A reference to blending or delivering a $G_n$ in tandem with a $G_O$ that does not explicitly specify a single $G_n$ and that can be understood to be a general case in which there is more than one added gas having the same or a different component gas of interest are meant to disclose this general case of the invention in which permutations and adaptations to accommodate more than one added component are understood to be related. Furthermore each of the general classes and specific embodiments of the invention are meant to refer back to the variety of aspects of the invention described herein and any logistical permutation of these various classes of and specific embodiments are understood to be described within the general concepts for implementing the invention elaborated above. Therefore, while a number of exemplary aspects and embodiments have been discussed above, those of skill in the art will recognize certain modifications, permutations, additions and sub-combinations thereof. It is therefore intended that the foregoing description and following appended claims and claims hereafter introduced are interpreted to include all such modifications, permutations, additions and sub-combinations as are within their true spirit and scope. Alternative terms for any features, elements, components etc of the invention as defined herein are not meant to be differentiated by virtue of the use of alternative language and each term is intended to be given its broadest meaning consistent with the context and the function it serves according the description of the invention as a whole. The scope of the claims should not be limited by the preferred embodiments, but should be given the broadest interpretation consistent with the description of the invention as a whole.

REFERENCE LIST

1. Prisman E, Slessarev M, Azami T, Nayot D, Milosevic M, Fisher J. Modified oxygen mask to induce target levels of hyperoxia and hypercarbia during radiotherapy: a more effective alternative to carbogen. Int J Radiat Biol 2007; 83(7):457-462.
2. Hoskin P J, Abdelath O, Phillips H et al. Inspired and expired gas concentrations in man during carbogen breathing. Radiother Oncol 1999; 51(2):175-177.
3. Mark C I, Slessarev M, Ito S, Han J, Fisher J A, Pike G B. Precise control of end-tidal carbon dioxide and oxygen improves BOLD and ASL cerebrovascular reactivity measures. Magn Reson Med 2010.
4. Mark C I, Fisher J A, Pike G B. Improved fMRI calibration: Precisely controlled hyperoxic versus hypercapnic stimuli. Neuroimage 2011; 54(2):1102-1111.
5. Slessarev M, Han J, Mardimae A et al. Prospective targeting and control of end-tidal CO2 and O2 concentrations. J Physiol 2007; 581(Pt 3):1207-1219.
6. Ito S, Mardimae A, Han J et al. Non-invasive prospective targeting of arterial P(CO2) in subjects at rest. J Physiol 2008; 586(Pt 15):3675-3682.

I claim:

1. A method for maintaining a targeted concentration $(DA_n^T)$ of a component $(DA_n)$ of an added gas $(G_n)$ over a time period, the added gas $(G_n)$ added to an inspiratory gas $(G_O)$ to formulate a respiratory gas $(G_R)$ for delivery to a subject, the method comprising:
    obtaining a first cumulative volume of at least one of the inspiratory gas $(G_O)$ and the respiratory gas $(G_R)$ flowed to the subject over an elapsed portion of the time period;
    obtaining a second cumulative volume of at least one of the added gas $(G_n)$ and the component $(DA_n)$ flowed to the subject over the elapsed portion of the time period;
    computing an error signal $(e_n)$ based on the first cumulative volume and the second cumulative volume, the error signal $(e_n)$ representing an adjusted volume of the added gas $(G_n)$ to be delivered over a remainder of the time period to maintain the targeted concentration $(DA_n^T)$ over the time period; and
    controlling, based on the error signal $(e_n)$, a gas delivery device to deliver the adjusted volume of the at least one added gas $(G_n)$ over the remainder of the time period to maintain the targeted concentration $(DA_n^T)$ over the time period.

2. The method of claim 1, wherein obtaining the first cumulative volume comprises:
    obtaining an incremental volume of the at least one of the inspiratory gas $(G_O)$ and the respiratory gas $(G_R)$ flowed to the subject over a most recent time interval;
    obtaining a previous cumulative volume of the at least one of the inspiratory gas $(G_O)$ and the respiratory gas $(G_R)$ flowed to the subject over a previously elapsed portion of the time period; and
    summing the previous cumulative volume and the incremental volume to obtain the first cumulative volume.

3. The method of claim 1, wherein obtaining the second cumulative volume comprises:
    obtaining an incremental volume of the at least one of the added gas $(G_n)$ and the component $(DA_n)$ flowed to the subject over a most recent time interval;
    obtaining a previous cumulative volume of the at least one of the added gas $(G_n)$ and the component $(DA_n)$ flowed to the subject over a previously elapsed portion of the time period; and
    summing the previous cumulative volume and the incremental volume to obtain the second cumulative volume.

4. The method of claim 1, wherein computing the error signal $(e_n)$ comprises:
    identifying successive time intervals of the remainder of the time period;
    computing incremental volumes of the added gas $(G_n)$ to be delivered over respective successive time intervals so that a total of the incremental volumes is the adjusted volume of the added gas $(G_n)$ to be delivered over the remainder of the time period; and
    computing the error signal $(e_n)$ for each of the successive time intervals, each respective error signal $(e_n)$ representing respective incremental volumes of the added gas $(G_n)$ to be delivered over the respective successive time intervals.

5. The method of claim 4, wherein computing the incremental volumes comprises computing one of an average and a weighted average of the incremental volumes to be delivered over the respective successive time intervals in the remainder of the time period.

6. The method of claim 1, wherein computing the error signal ($e_n$) is based on (i) a current ratio of the first cumulative volume and the second cumulative volume and (ii) a cumulative volume of respiratory gas ($CVG_R$) including the adjusted volume of the at least one added gas ($G_n$) to be delivered over the remainder of the time period.

7. A system for maintaining a targeted concentration ($DA_n^T$) of a component ($DA_n$) of an added gas ($G_n$) over a time period, the added gas ($G_n$) added to an inspiratory gas ($G_O$) to formulate a respiratory gas ($G_R$) for delivery to a subject, the system comprising:
   a delivery conduit to deliver the respiratory gas ($G_R$) to the subject;
   an inspiratory gas source coupled to the delivery conduit to supply the inspiratory gas ($G_O$) to the delivery conduit;
   an inspiratory volume sensor to detect volumes of one of the inspiratory gas ($G_O$) and the respiratory gas ($G_R$) flowed to the subject;
   an added gas source coupled to the delivery conduit via an added gas conduit to supply the added gas ($G_n$) to the delivery conduit;
   a gas delivery means along the added gas conduit to control a flow of the added gas ($G_n$) to the delivery conduit;
   an added gas volume sensor to detect volumes of the at least one of the added gas ($G_n$) and the component ($DA_n$) flowed to the subject;
   a controller operatively coupled to the inspiratory volume sensor, the added gas volume sensor, and the gas delivery means, the controller to:
      obtain a first cumulative volume of at least one of the inspiratory gas ($G_O$) and the respiratory gas ($G_R$) flowed to the subject over an elapsed portion of the time period;
      obtain a second cumulative volume of at least one of the added gas ($G_n$) and the component ($DA_n$) flowed to the subject over the elapsed portion of the time period;
      compute an error signal ($e_n$) based on the first cumulative volume and the second cumulative volume, the error signal ($e_n$) representing an adjusted volume of the added gas ($G_n$) to be delivered over a remainder of the time period to maintain the targeted concentration ($DA_n^T$) over the time period; and
      control, based on the error signal ($e_n$), the gas delivery means to deliver the adjusted volume of the at least one added gas ($G_n$) over the remainder of the time period to maintain the targeted concentration ($DA_n^T$) over the time period.

8. The system of claim 7, wherein the inspiratory volume sensor is disposed along the delivery conduit upstream of the added gas conduit.

9. The system of claim 8, further comprising a cross-bridge connecting an inspiratory conduit with an expiratory conduit of the delivery conduit, the cross-bridge to cause the inspiratory volume sensor to detect only volumes of gas destined for inspiration by the subject.

10. The system of claim 7, wherein the inspiratory volume sensor is disposed along the delivery conduit downstream of the added gas conduit, proximal to a patient connection of the delivery conduit.

11. The system of claim 7, wherein the gas delivery means is one of: a proportional flow control valve and a solenoid valve.

12. The system of claim 7, wherein to obtain the first cumulative volume, the controller is to:
   obtain, from the inspiratory volume sensor, an incremental volume of the at least one of the inspiratory gas ($G_O$) and the respiratory gas ($G_R$) flowed to the subject over a most recent time interval;
   obtain a previous cumulative volume of the at least one of the inspiratory gas ($G_O$) and the respiratory gas ($G_R$) flowed to the subject over a previously elapsed portion of the time period; and
   sum the previous cumulative volume and the incremental volume to obtain the first cumulative volume.

13. The system of claim 7, wherein to obtain the second cumulative volume, the controller is to:
   obtain, from the added gas volume sensor, an incremental volume of the at least one of the added gas ($G_n$) and the component ($DA_n$) flowed to the subject over a most recent time interval;
   obtain a previous cumulative volume of the at least one of the added gas ($G_n$) and the component ($DA_n$) flowed to the subject over a previously elapsed portion of the time period; and
   sum the previous cumulative volume and the incremental volume to obtain the second cumulative volume.

14. The system of claim 7, wherein to compute the error signal ($e_n$), the controller is to:
   identify successive time intervals of the remainder of the time period;
   compute incremental volumes of the added gas ($G_n$) to be delivered over respective successive time intervals so that a total of the incremental volumes is the adjusted volume of the added gas ($G_n$) to be delivered over the remainder of the time period; and
   compute the error signal ($e_n$) for each of the successive time intervals, each respective error signal ($e_n$) representing respective incremental volumes of the added gas ($G_n$) to be delivered over the respective successive time intervals.

15. The system of claim 14, wherein to compute the incremental volumes, the controller is to compute one of an average and a weighted average of the incremental volumes to be delivered over the respective successive time intervals in the remainder of the time period.

16. The system of claim 7, wherein the controller is to compute the error signal ($e_n$) based on (i) a current ratio of the first cumulative volume and the second cumulative volume and (ii) a cumulative volume of respiratory gas ($CVG_R$) including the adjusted volume of the at least one added gas ($G_n$) to be delivered over the remainder of the time period.

* * * * *